(12) United States Patent
Nakamura et al.

(10) Patent No.: US 10,829,522 B2
(45) Date of Patent: Nov. 10, 2020

(54) PEPTIDE INHIBITING COLONIZATION BY PATHOGENIC BACTERIA, AND COLONIZATION INHIBITOR INCLUDING SAME

(71) Applicants: OSAKA UNIVERSITY, Osaka (JP); BIKENBIOMICS CO., LTD, Osaka (JP)

(72) Inventors: Shota Nakamura, Suita (JP); Kazuki Kawahara, Suita (JP); Hiroya Oki, Suita (JP); Takuya Yoshida, Suita (JP); Tadayasu Ohkubo, Suita (JP); Yuji Kobayashi, Suita (JP); Takahiro Maruno, Suita (JP); Daisuke Motooka, Suita (JP); Shigeaki Matsuda, Suita (JP); Toshio Kodama, Suita (JP); Tetsuya Iida, Suita (JP); Yasumitsu Tsujino, Ibaraki (JP); Shunsuke Fukakusa, Ibaraki (JP)

(73) Assignees: OSAKA UNIVERSITY, Osaka (JP); BIKENBIOMICS CO., LTD., Osaka (JP)

(*) Notice: Subject to any disclaimer, the term of this patent is extended or adjusted under 35 U.S.C. 154(b) by 0 days.

(21) Appl. No.: 16/097,219

(22) PCT Filed: Apr. 25, 2017

(86) PCT No.: PCT/JP2017/016284
§ 371 (c)(1),
(2) Date: Feb. 25, 2019

(87) PCT Pub. No.: WO2017/188215
PCT Pub. Date: Nov. 2, 2017

(65) Prior Publication Data
US 2019/0284246 A1    Sep. 19, 2019

(30) Foreign Application Priority Data
Apr. 27, 2016  (JP) .................. 2016-089902

(51) Int. Cl.
*A61K 38/16* (2006.01)
*A61K 38/00* (2006.01)
*C07K 14/00* (2006.01)
*C12N 15/00* (2006.01)
*C12N 15/09* (2006.01)
*C07K 14/245* (2006.01)

(52) U.S. Cl.
CPC ............ *C07K 14/245* (2013.01); *A61K 38/16* (2013.01); *C12N 15/00* (2013.01); *C12N 15/09* (2013.01); *A61K 38/00* (2013.01)

(58) Field of Classification Search
CPC ...... A61K 38/00; A61K 38/16; C07K 14/245; C07K 14/00; C07K 2319/73; C12N 15/00; C12N 15/09

USPC ................................. 530/300, 324
See application file for complete search history.

(56) References Cited

U.S. PATENT DOCUMENTS

| | | | | |
|---|---|---|---|---|
| 5,674,492 | A * | 10/1997 | Armitage ............. | C07K 14/705 424/144.1 |
| 6,211,338 | B1 * | 4/2001 | Malcolm ............. | C07K 14/005 435/219 |
| 7,504,490 | B1 * | 3/2009 | Weinstock ............ | C07K 14/38 435/252.3 |
| 7,569,389 | B2 * | 8/2009 | Feldmann ............ | C07K 14/415 435/419 |
| 8,785,374 | B2 * | 7/2014 | Tamiz .................. | A61K 38/08 514/1.5 |
| 9,073,990 | B2 * | 7/2015 | Paas ................... | B82Y 5/00 |
| 9,518,277 | B2 * | 12/2016 | Franklin .............. | C12N 15/52 |
| 10,040,842 | B2 * | 8/2018 | Jacobs ................. | C07K 14/78 |
| 10,184,131 | B2 * | 1/2019 | Maor ................. | C12N 15/8261 |
| 2012/0276146 | A1 | 11/2012 | Holmgren | |

FOREIGN PATENT DOCUMENTS

JP    2013-505017 A    2/2013

OTHER PUBLICATIONS

Pearson WR, "An Introduction to Sequence Similarity ("Homology") Searching," Current Protocols in Bioinformatics, 3.1.1-3.1.8. (Year: 2013).*

Kanduc D, "Homology, similarity, and identity in peptide epitope immunodefinition," Journal of Peptide Science, 18: 487-494. (Year: 2012).*

Yampolsky et al., "The Exchangeabiilty of Amino Acids in Proteins," Genetics, 170: 1459-1472. (Year: 2005).*

Kawahara, K., et al., Homo-trimeric Structure of the Type IVb Minor Pilin CofB Suggests Mechanism of CFA/III Pilus Assembly in Human Enterotoxigenic *Escherichia coli*, Journal of Molecular Biology, vol. 428, pp. 1209-1226, 2016.

Oki, H, et al., Interplay of a secreted protein with type IVb pilus for efficient enterotoxigenic *Escherichia coli* colonization, Proceedings of the National Academy of Sciences (PNAS), vol. 115, No. pp. 7422-7427, 2018.

(Continued)

*Primary Examiner* — Julie Ha
(74) *Attorney, Agent, or Firm* — Knobbe, Martens, Olson & Bear, LLP

(57) ABSTRACT

A peptide capable of preventing pathogenic bacteria from colonizing in digestive organs comprises a first domain having an amino acid sequence capable of binding to a minor pilin of IVb fimbriae, and a second domain having an amino acid sequence capable of multimerization, the second domain connect to the first domain via a linker sequence.

10 Claims, 10 Drawing Sheets

Specification includes a Sequence Listing.

(56) References Cited

OTHER PUBLICATIONS

Extended European Search Report, dated Oct. 31, 2019, in EP Patent Application No. 17789497.9.
Boudko, S.P., et al., Crystal Structure of Human Collagen XVIII Trimerization Domain: A Novel Collagen Trimerization Fold, Journal of Molecular Biology, vol. 392, No. 3, pp. 787-802, 2009.
Brodsky, B., et al., Triple-Helical Peptides: An Approach to Collagen Conformation, Stability, and Self-Association, Biopolymers, vol. 89, No. 5, pp. 345-353, 2008.
Eckert, D.M., et al., Design of potent inhibitors of HIV-1 entry from the gp41 N-peptide region, PNAS, vol. 98, No. 20, pp. 11187-11192, 2001.
Güthe, S., et al., Very Fast Folding and Association of a Trimerization Domain from Bacteriophage T4 Fibritin, Journal of Molecular Biology, vol. 337, No. 4, pp. 905-915, 2004.
Harbury, P.B., et al., Crystal structure of an isoleucine-zipper trimer, Nature, vol. 371, pp. 80-83, 1994.
Wirz, J.A., et al., Crystal structure of the human collagen XV trimerization domain: A potent trimerizing unit common to multiplexin collagens, Matrix Biololgy, vol. 30, No. 1, pp. 9-15, 2011.
Abe, H., et al., Isolation and Characterization of Enterotoxigenic *Escherichia coli* From Patients with Traveler's Diarrhoea in Osaka, Journal of Diarrhoeal Diseases Research, vol. 2, No. 2, pp. 83-87, 1984.
Fleckenstein, J.M., et al., Interaction of an Outer Membrane Protein of Enterotoxigenic *Escherichia coli* with Cell Surface Heparan Sulfate Proteoglycans, Infection and Immunity, vol. 70, No. 3, pp. 1530-1537, 2002.
Fleckenstein, J.M., et al., Molecular mechanisms of enterotoxigenic *Escherichia coli* infection, Microbes and infection, vol. 12, pp. 89-98, 2010.

International Search Report, dated Aug. 1, 2017, in International Application No. PCT/JP2017/016284.
Kirn, T.J., et al., Secretion of a soluble colonization factor by the TCP type 4 pilus biogenesis pathway in Vibrio cholerae, Molecular Microbiology, vol. 49, No. 1, pp. 81-92, 2003.
Kolappan, S., et al., Crystal structure of the minor pilin CofB, the initiator of CFA/III pilus assembry in enterotoxigenic *Escherichia coli*, The Journal of Biological Chemistry, vol. 290, No. 43, pp. 25805-25818, 2015.
Kolappan, S., et al., Structural characterization of CFA/III and Longus type IVb pili from enterotoxigenic *Escherichia coli*, Journal of Bacteriology, vol. 194, No. 10, pp. 2725-2735, 2012.
Madhavan, T.P.V., et al., Colonization Factors of Enterotoxigenic *Escherichia coli*, Advances in Applied Microbiology, vol. 90, pp. 155-197, 2015.
Von Mentzer, A., et al., Identification of enterotoxigenic *Escherichia coil* (ETEC) clades with long-term global distribution, Nature Genetics, vol. 46, No. 12, pp. 1321-1328, 2014.
Qadri, F., et al., Enterotoxigenic *Escherichia coli* in Developing Countries: Epidemiology, Microbiology, Clinical Features, Treatment, and Prevention, Clinical Microbiology Reviews, vol. 18, No. 3, pp. 465-483, 2005.
Roy, K., et al., Enterotoxigenic *Escherichia coli* EtpA mediates adhesion between flagella and host cell, Nature, vol. 457, pp. 594-599, 2009.
Sjöling, Å., et al., Implications of enterotoxigenic *Escherichia coli* genomics for vaccine development, Expert Review of Vaccines, vol. 14, No. 4, pp. 551-560, 2015 (Published Online 2014).
Yuen, A.S.W., et al., Structure andsecretion of CofJ, a putative colonization factor of enterotoxigenic *Escherichia coli*, Molecular Microbiology, vol. 90, No. 4, pp. 898-918, 2013.
Notice of Reasons for Refusal, dated Jun. 2, 2020, in Japanese Patent Application No. 2018-514605.

* cited by examiner

[FIG.1]
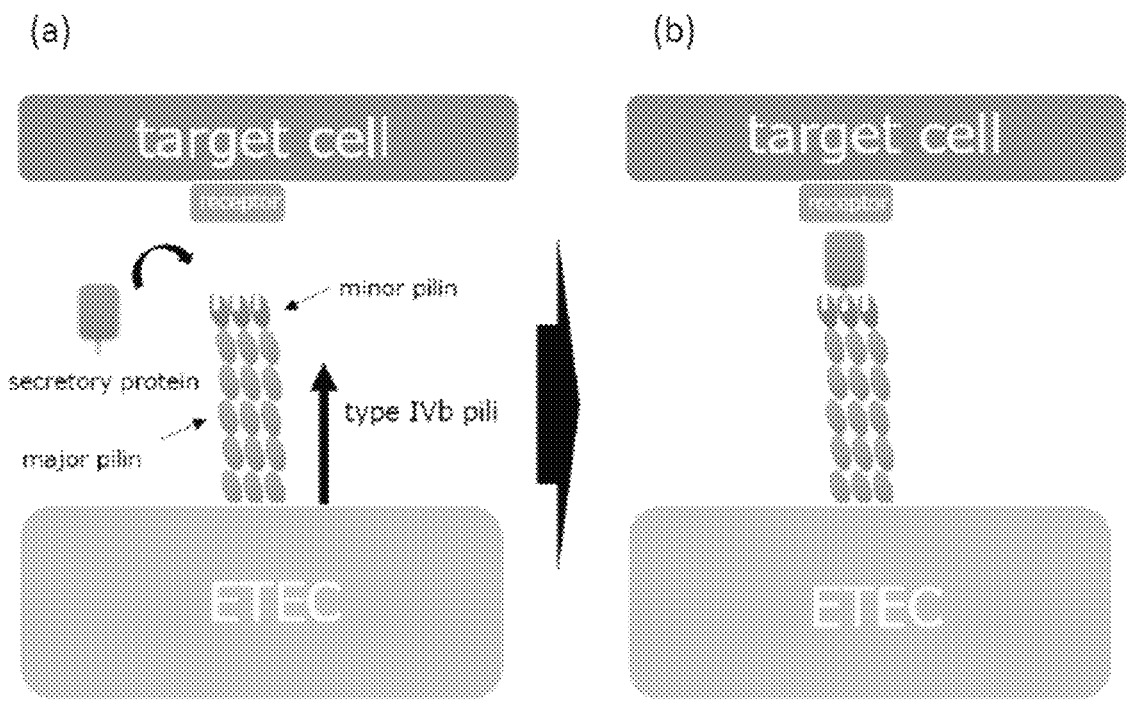

[FIG.2]
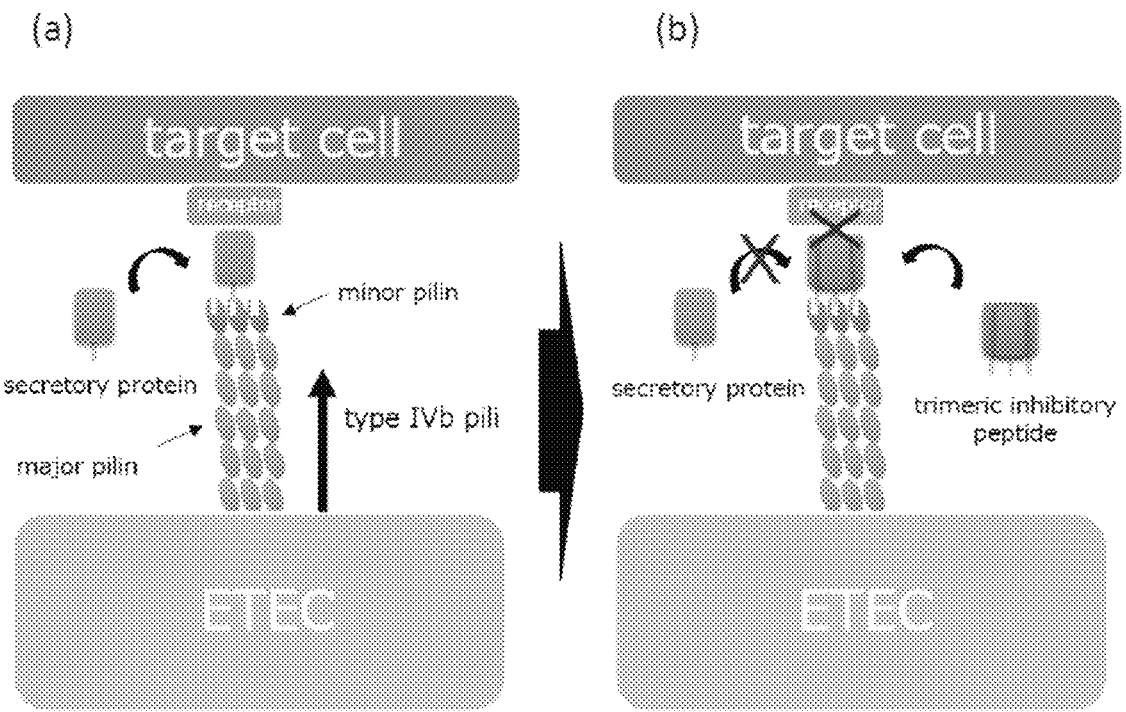
[FIG.3]
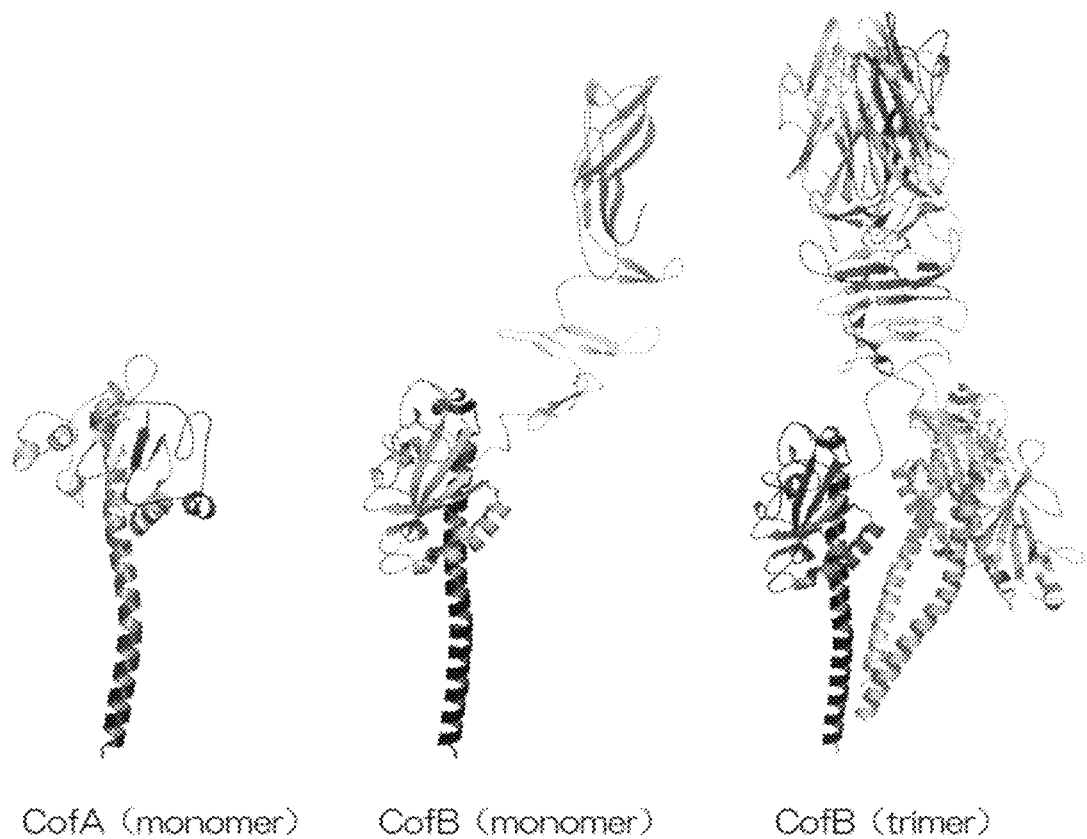
CofA (monomer)   CofB (monomer)   CofB (trimer)

[FIG.4]
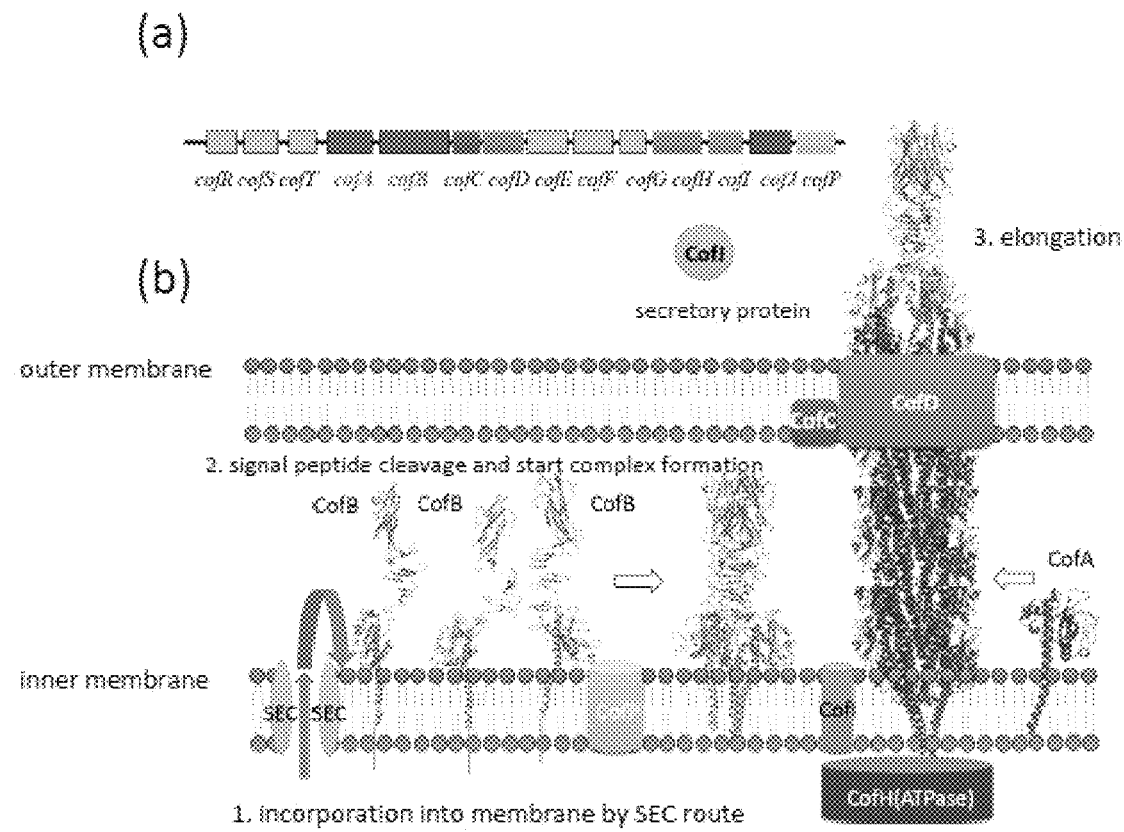
[FIG.5]
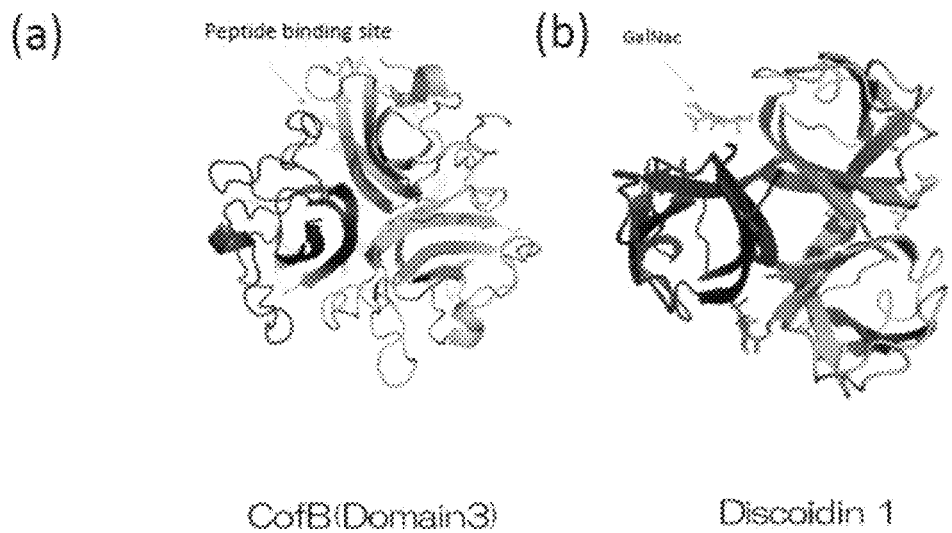

[FIG.6]
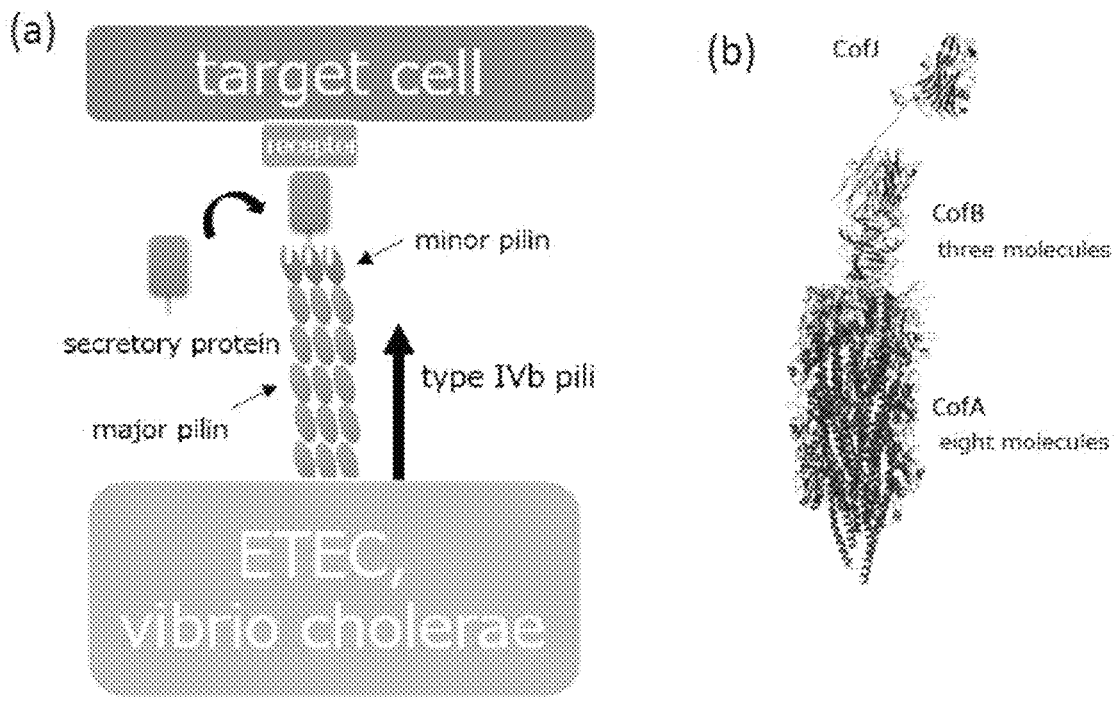
[FIG.7]
CofJ$^{1-24}$: complex of S (1) PSSEGGAFTVNMPKTSTVDDIR (24) and CofB
SEQ ID NO:1
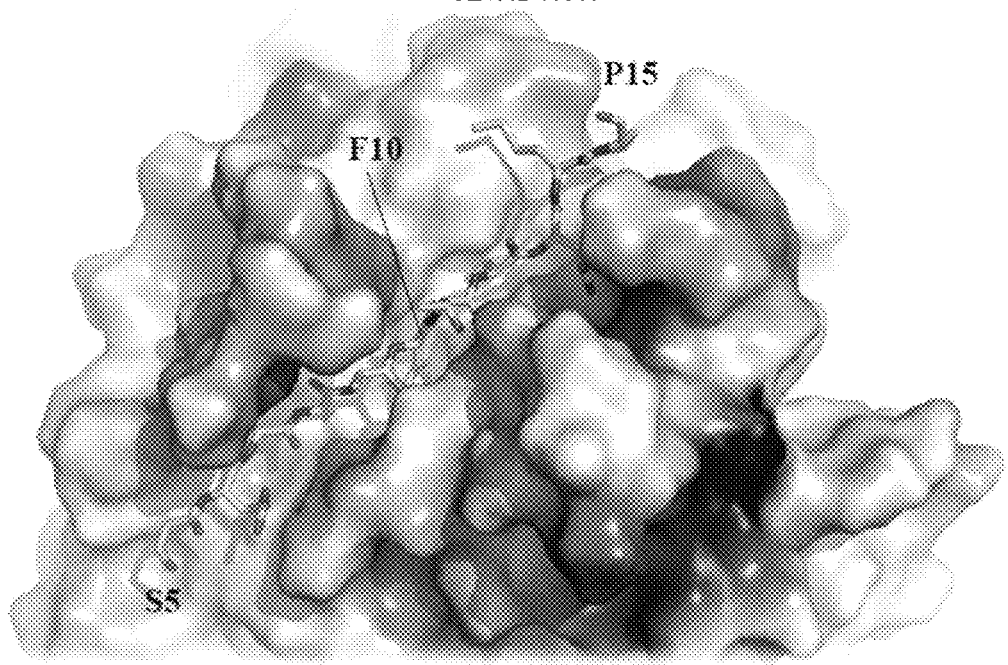

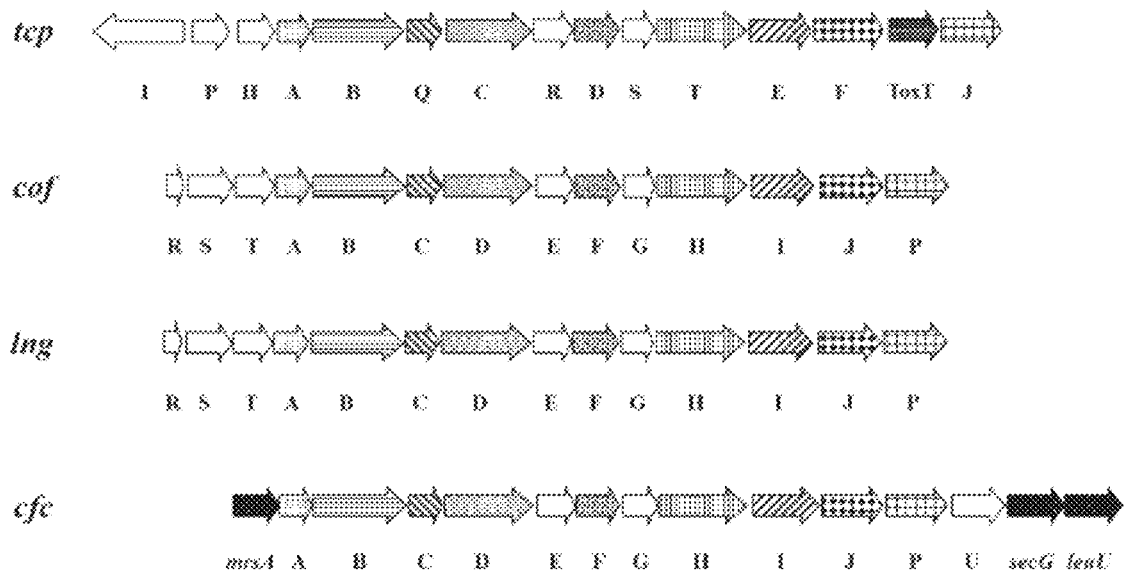

[FIG.10]
(a) over all structure
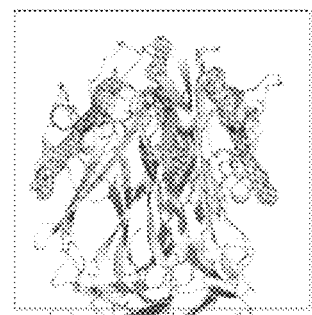
(b)
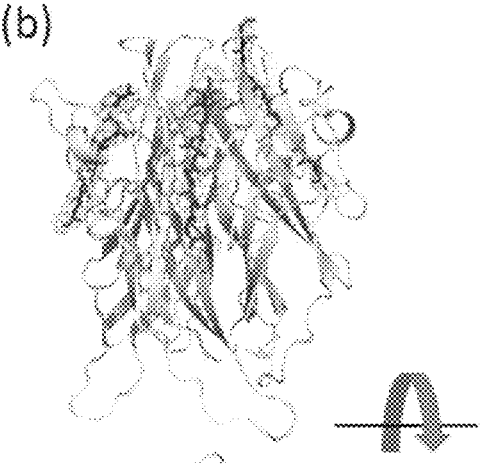
(c)

[FIG.11]
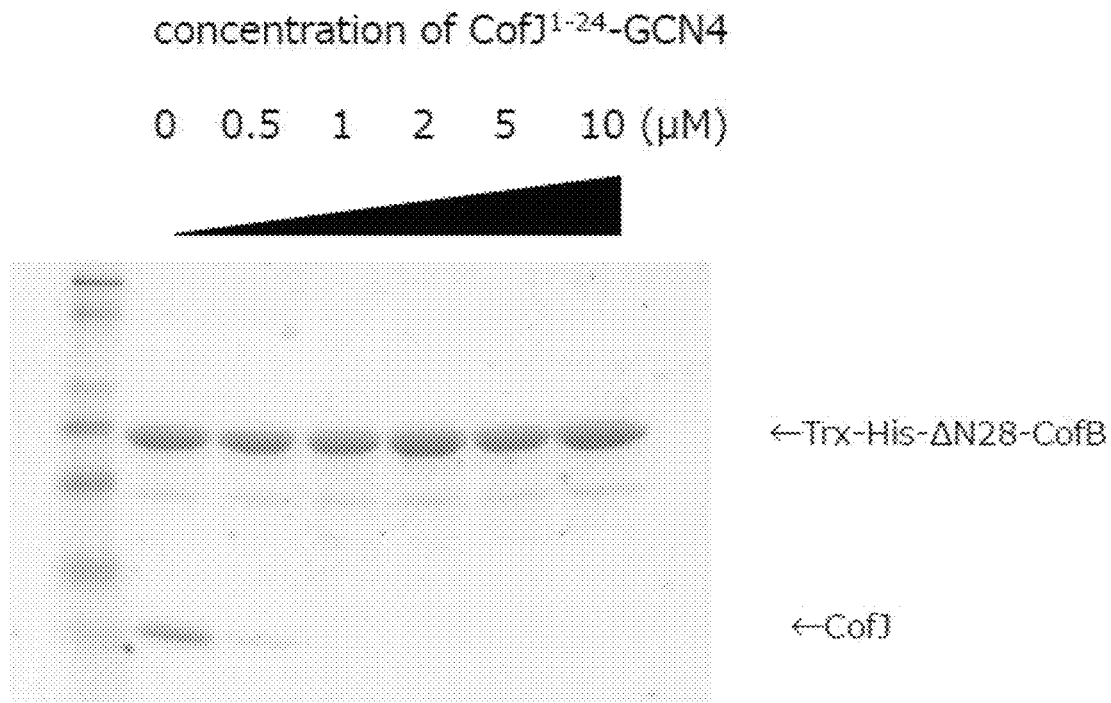
[FIG.12]
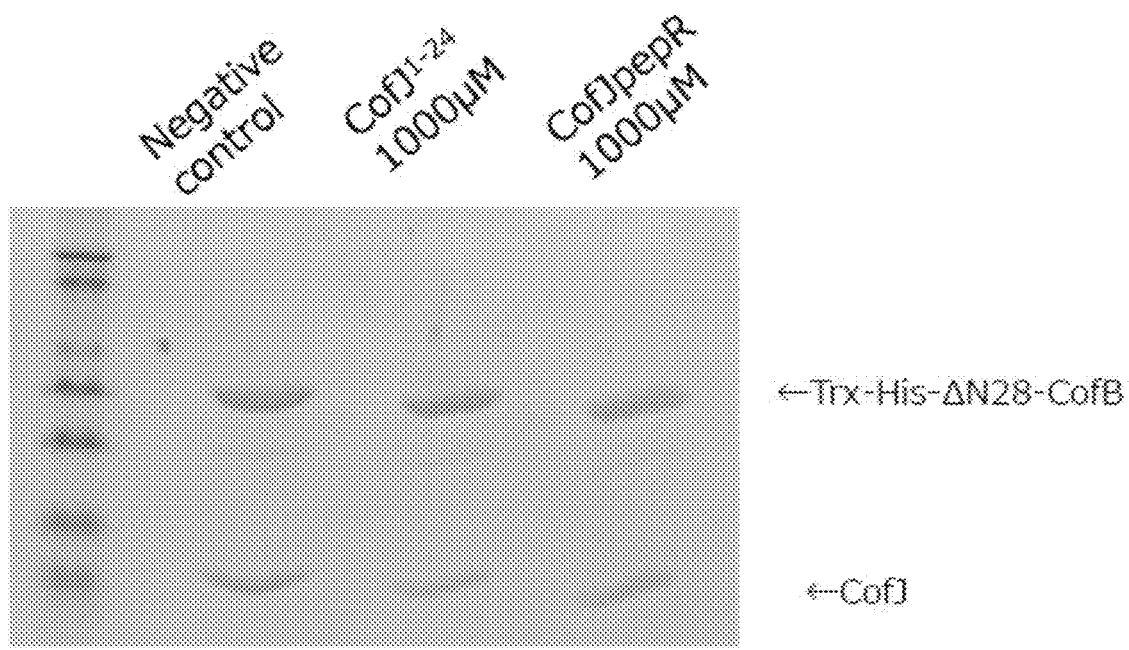

[FIG.13]
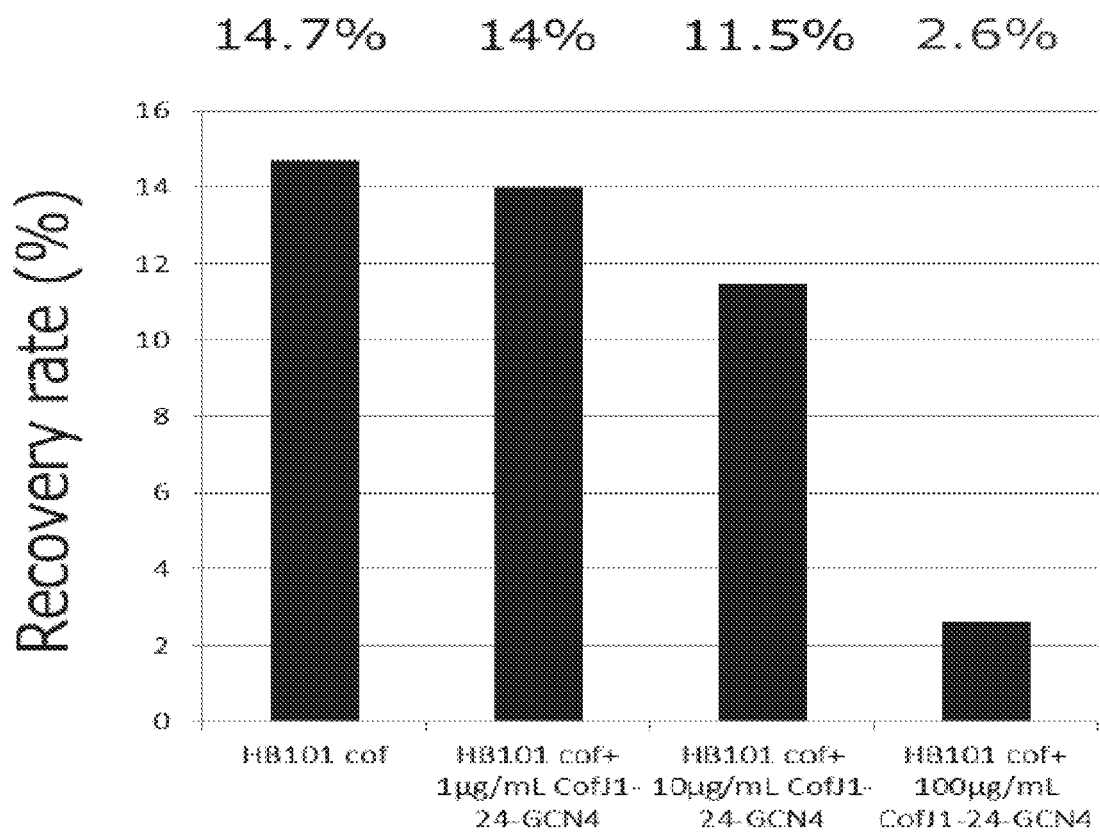

[FIG.14]
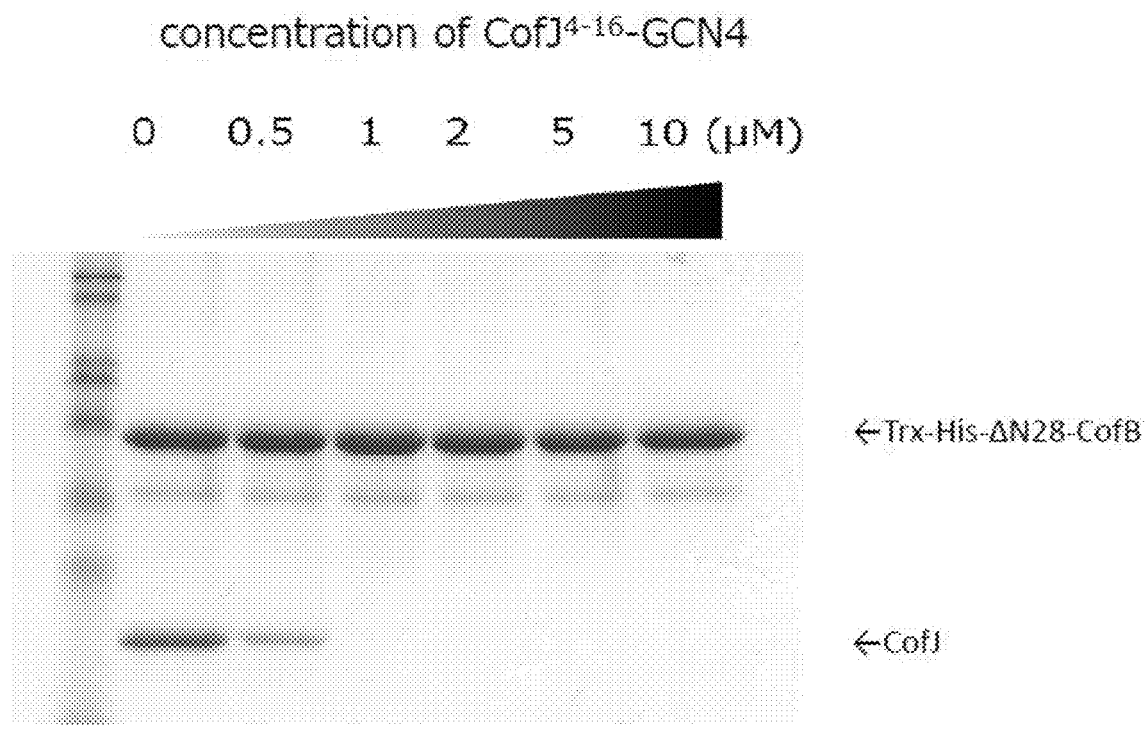

[FIG.15]
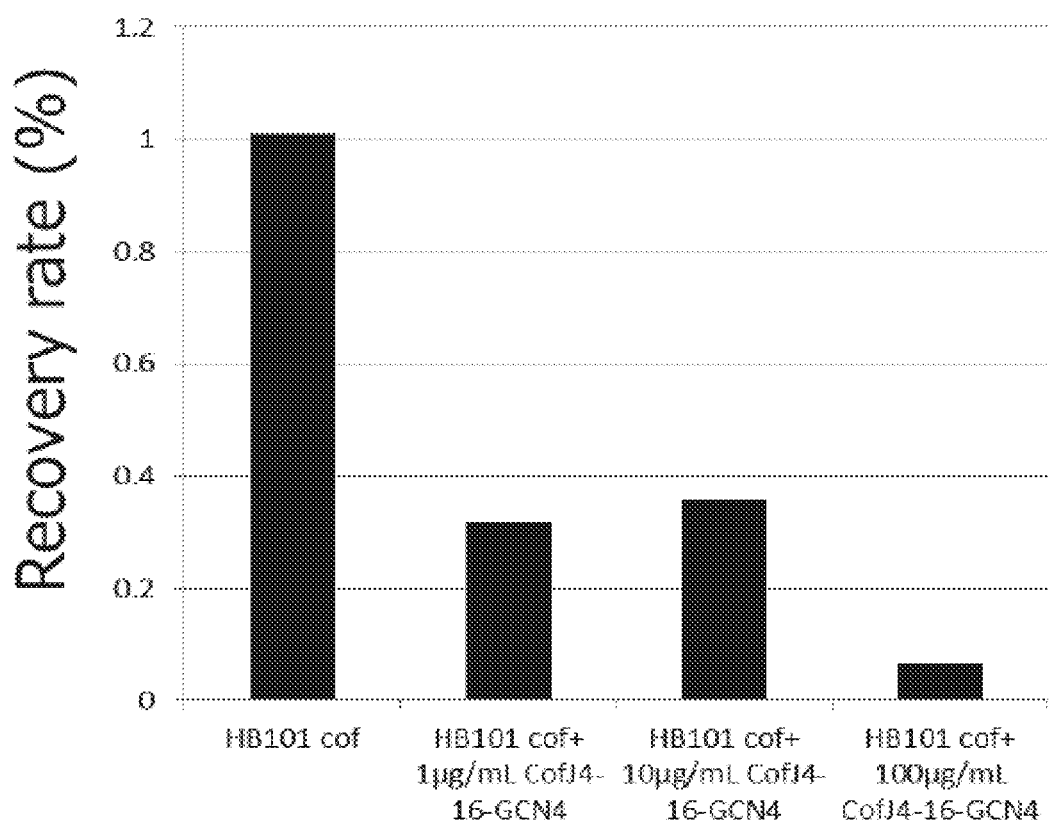

PEPTIDE INHIBITING COLONIZATION BY PATHOGENIC BACTERIA, AND COLONIZATION INHIBITOR INCLUDING SAME

CROSS REFERENCE TO RELATED APPLICATIONS

This application is the U.S. National Stage Application under 35 U.S.C. § 371 of International Application No. PCT/JP2017/016284, filed Apr. 25, 2017, designating the U.S. and published as WO 2017/188215 A1 on Nov. 2, 2017, which claims the benefit of Japanese Patent Application No. JP 2016-089902, filed Apr. 27, 2016. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled CPJ007001APCSEQLIST.txt, created and last saved on Oct. 19, 2018, which is 5,761 bytes in size. The information in the Electronic Sequence Listing is incorporated herein by reference in its entirety in accordance with 35 U.S.C. § 1.52(e).

TECHNICAL FIELD

The present invention relates to novel peptides, more particularly to peptides that inhibit colorization of pathogenic bacteria in digestive organs and a colonization inhibitor containing the peptide.

BACKGROUND

In recent years, a number of pathogenic bacteria that cause diseases of digestive organs have been revealed. For example, enterotoxigenic *Escherichia coli* (ETEC) which is a type of pathogenic bacteria with intestinal toxicity is known to invade the digestive tract of humans through water or food and cause cholera like diarrhea. Infectious diseases by ETEC have become a serious problem among people living in developing countries and travelers visiting the the region, and it is estimated that about 200 million people a year are infected in the world and approximately 380,000 people including mainly infants under 5 years old will die (Non-Patent Document 1). A statistical survey conducted at the quarantine station in Osaka airport in Japan reported that about 8% of Japanese travelers who developed diarrhea are infected with ETEC (Non-Patent Document 2).

As a first step in the pathogenic expression of ETEC, it must adhere to the small intestinal epithelial cells and colonize there, and colonization factors (CFs) play its role. To date, at least twenty five CFs such as colonization factor antigen 1 (CFA/I), *E. coli* surface antigen 1 (CS1), presumed colonization factor 071 (PCF071) and the like have been reported (Non-Patent Document 3). By the action of these pathogenic factors, when ETEC adheres to the small intestinal epithelial cells of the host, it forms biofilms, microcolonies and the like and colonizes there. Thereafter, as a second step, ETEC produces heat-labile intestinal toxin (LT) or heat-resistant intestinal toxin (ST) and develops pathogenicity.

Almost all of CFs that ETEC has are ciliary colonization factors, and classified into several groups depending on the amino acid sequence of the constituent component and the feature of immunogenicity or the like (Non-patent document 3). For example, CFA/I, CS1, CS2, CS4, CS5, CS7, CS14, CS17, CS19 and PCF071 form pili belonging to the class type 5, while CS12, CS18, CS20, CS26, CS27 and CS28 form pili belonging to the class type 1b. In addition to these, CS13, CS15, CS22 and CS23, or CS3 and CS6 are similarly grouped, respectively. The structures and natures of these CFs are still unknown in many respects, but these CFs have similar constituent components and are mainly constituted of Chaperon proteins present in the *E. coli* periplasm, pilus main constituent subunits (major pilin), a small number of subunits contained in the pilus (minor pilin) and outer membrane Usher proteins, and pili are formed by the Chaperon-Usher path (Non-patent document 3). In contrast, CFA/III (CS8) and Longus (CS21) form pili classified as type IV, and the pilus structure and the pilus forming mechanism different from those by the Chaperon-Usher pathway are provided. CS10 and CS11 have been reported as other CFs, but the pilus structures of them are still unknown in many respects.

An outer membrane protein Tia identified from the ETEC H10407 strain is known as a non-ciliary colonization factor expressed by ETEC, and the protein binds to proteoglycan on the host cell surface (Non-Patent Document 4). In addition, also EtpA identified from ETEC H10407 strain is known as a non-ciliary colonization factor expressed by ETEC. It has been suggested that EtpA binds to a highly conserved region of the flagellin protein and may bridge the microbial body and the host cell surface (Non-Patent Document 5).

Generally, each strain of ETEC possesses 1 to 3 kinds of CFs and also possess various secretory colonization factors (Non-Patent Document 6). Therefore, development of treatment means such as vaccination is difficult for reasons such as diversity of the spatial and temporal expression control mechanism in accordance with the environments around each CFs, further, introduction of strain-dependent variations into the surface antigen, and the like, in addition to the complexity of the combination. Currently, as candidate antigens for vaccine development, toxin LT produced by almost all ETECs is considered, but due to its toxicity, there is a restriction on the dose in oral administration or the like, and in recent years, a variant obtained by substituting the amino acid at the active site has been studied as an alternative antigen. Similar use is considered also for ST, but it is a problem that the molecular size (peptide consisting of about 20 residues) is small and it is difficult to cause an immune response (Non-Patent Document 7). Development of a vaccine using each colonization factor as an antigen has also been advanced. Because it is necessary to devise to cause broad immune, the current most effective vaccine is a live or inactivated ETEC vaccine using CFA/I, CS3, CS5, CS6, and a strain producing intestinal toxin LT (Non-patent Document 7 and 8). These vaccines are applicable to each group of pili primarily formed by the Chaperon-Usher pathway and are believed to represent the effect on 80% of the clinical strains of ETEC.

REFERENCES

[Non-Patent Literature 1] Qadri, F. et al. Clin. Microbiol. Rev. 2005, 18, 465-483.

[Non-Patent Literature 2] Abe, H. et al. J. Diar. Dis. Res. 1984, 2, 83-87.

[Non-Patent Literature 3] Madhavan, T. V. et al. Adv. Appl. Microbiol. 2015, 90, 155-197.
[Non-Patent Literature 4] Fleckenstein, J. M. et al. Infect. Immun 2002, 70, 1530-1537.
[Non-Patent Literature 5] Roy, K. et al. Nature 2009, 457, 594-598.
[Non-Patent Literature 6] Mentzer, A. et al. Nat. Genetics 2014, 46, 1321-1326.
[Non-Patent Literature 7] Sjoling, A. et al. Expert Rev. Vaccines 2015, 4, 551-560.
[Non-Patent Literature 8] Fleckenstein, J. M. et al. Microbes and infections 2010, 12, 89-98.

SUMMARY

Effective ETEC vaccines have not been developed to date. Studies of live or inactivated ETEC vaccines using CFA/I, CS3, CS5, CS6, and a strain producing intestinal toxin LT, as the most promising vaccine candidates, are progressing. However, there is no effect against strains of ETEC containing colonization factors or toxins not contained in this vaccine. In particular, it is not suitable for strains which form type IV pili and produce CFs having different pilus structures and characteristics from CFs contained in the above-described inactivated vaccines. Particularly, longus (CS21) has been identified from ETECs in a wide area and is prevalent in regions including Latin America, Middle East and North Africa (Isidean S D et al. Vaccine 2011, 29, 6167-6178). With the above-described inactivated vaccine, it is difficult to inhibit infection of strains carrying such colonization factors. There is also a concern that inactivation of strains does not cause immunity to secretory pathogenic factors, and there is also a problem that it is difficult to induce long-term immunity. To solve these problems, it is considered to identify highly conserving protein expressing on the surface of the broad ETEC and to produce a vaccine using this protein as an antigen, however, such proteins have not been discovered yet.

Thus, it is thought to be realistic and more effective to perform immunization with multiple antigens by revealing the details of the structure and colonizing mechanism of the colonization factors of ETEC at the molecular level and identifying conserved epitopes, rather than searching and identification of the protein. In addition, if the colonizing mechanism becomes clear, development of a colonization inhibitor is also possible.

The present invention has been made in view of the above problems, and an object thereof is to be able to prevent bacteria having a colonization factor from colonizing in digestive organs.

The present inventors have intensively studied and resultantly found a mechanism in which particularly pathogenic bacteria that produce type IVb pili, among bacteria, colonize in digestive organs and succeeded in producing a novel peptide that inhibits colonization of the bacteria, based on the mechanism.

Specifically, the peptide according to the present invention is characterized by comprising a first domain having an amino acid sequence capable of binding to minor pilin of type IVb pili, and a second domain having an amino acid sequence connected via a linker sequence to the first domain and capable of multimerizing.

Bacteria producing type IVb pili become able to adhere to and colonize on the target cell by bonding of secretory proteins generated by the bacteria themselves to secretory protein binding sites of minor pilin located at the top of the major constituent subunit (major pilin) of type IVb pili, though the bacteria are unable to bind to the receptor of target cell in digestive organs and the like only by the pili. In contrast, the peptide according to the present invention can bind to type IVb pili since the peptide has a first domain having an amino acid sequence capable of binding to the secretory protein binding site of minor pilin of type IVb pili. Thus, the peptide according to the present invention inhibits the bonding of secretory proteins and type IVb pili of bacteria, by binding to type IVb pili, and resultantly can inhibit the bacteria from adhering to and colonizing on the target cell in digestive organs and the like. Usually type IVb pili form a homotrimer, while the peptide according to the present invention has a second domain capable of multimerizing, hence, the peptide is able to bind simultaneously to all the binding sites of the homotrimer. Therefore, it is possible to efficiently inhibit the bonding between the secretory proteins of the bacteria and type IVb pili, and resultantly it is possible to efficiently inhibit the bacteria from adhering to and colonizing on the target cell in digestive organs and the like. This anti-adhesion mechanism has very little effect on the host since the peptide selectively binds to pathogenic bacteria rather than binding to receptors on host cells and then elimination outside the host is elicited. Also, unlike antibiotics, pathogenic bacteria are not killed, thus, selection pressures are small and it is possible to suppress the appearance of drug-resistant bacteria. Inhibitors focusing on such anti-adhesion mechanism have been studied for type I pili and type P pili carried by uropathogenic *Escherichia coli* (UPEC) (Sharon, N. Biochim Biophys. Acta 2006, 1760, 527-537). Both are pili having a lectin domain that recognizes a sugar chain at the tip, and the development of sugar derivatives and the like that specifically bind to the sugar chain binding region thereof is advancing. Regarding ETEC, an antiadhesive agent in which a sugar chain is bound to nanoparticles has been studied (Ravel, Y. S. et al. Nanoscale 2015, 7, 8326-8331). However, since the adhesion mechanism via pili is not clear, inhibitors that efficiently inhibit adhesion of type IVb pili have not been developed ever.

In the peptide according to the present invention, it is preferable that the first domain has an amino acid sequence having homology of 70% or more with any sequence of SEQ ID NOS: 1 to 4.

SEQ ID NOS: 1 to 4 are sequences involved in binding to the binding sites of miner pilin (CofB, LngB, CfcB and TcpB) corresponding to secretory proteins such as CofJ, LngJ, CfcJ and TcpF expressed by bacteria that produce type IVb pili. Therefore, it is possible to inhibit the binding of the secretory protein to the type IVb pili, by including the first domain having high homology with these. Further, it is particularly preferable that the first domain consists of the sequence of any one of SEQ ID NOS: 1 to 4.

In the peptide according to the present invention, it is preferable that the first domain has the sequence of SEQ ID NO: 5.

SEQ ID NO: 5 is a sequence strongly involved in binding to the binding site of the minor pilin (CofB) in the amino acid sequence of CofJ. Therefore, when the first domain has the sequence of SEQ ID NO: 5, the peptide according to the present invention can efficiently inhibit the binding between CofJ and minor pilin (CofB). In addition, by configuring the first domain only with the sequence of SEQ ID NO: 5, the first domain can be made shorter and the structure can be simplified.

In the peptide according to the present invention, it is preferable that the first domain has the sequence of SEQ ID NO: 23.

SEQ ID NO: 23 is a sequence in which serine is added to the N terminal side of the above SEQ ID NO: 5 and lysine is added to the C terminal side, and when the first domain has the sequence of SEQ ID NO: 23, the peptide according to the present invention can efficiently inhibit the binding between CofJ and minor pilin (CofB) as in the case of SEQ ID NO: 5 above. In addition, by configuring the first domain only with the sequence of SEQ ID NO: 23, the first domain can be made shorter and the structure can be simplified.

In the peptide according to the present invention, the second domain preferably contains an amino acid sequence capable of trimerizing.

Since the type IVb pilus forms a homotrimer as described above, when the second domain contains the amino acid sequence capable of trimerizing, the peptide of the present invention can bind to the binding sites in all minor pilins in the homotrimer. This can effectively inhibit the binding between secretory proteins of bacteria and type IVb pili.

In the peptide of the present invention, the second domain preferably has the amino acid sequence of SEQ ID NO: 6, or an amino acid sequence repeating 4 to 10 times the amino acid sequence of SEQ ID NO: 7 or SEQ ID NO: 8.

SEQ ID NO: 6 is a sequence that forms a GCN4 trimeric coiled-coil, and the amino acid sequence repeating 4 to 10 times the sequence of SEQ ID NO: 7 or SEQ ID NO: 8 is a sequence that forms a collagen-like triple helical structure, that is, a sequence that promotes peptide trimerization. Therefore, by providing the second domain having such an amino acid sequence, the peptide of the present invention can form a trimer. Therefore, by adopting these sequences, it is possible to obtain a peptide capable of efficiently inhibiting the binding between the bacterial secretory proteins and the type IVb pili as described above.

In addition, in the peptide according to the present invention, the linker sequence may be SEQ ID NO: 9.

The colonization inhibitor according to the present invention is one which inhibits colonization of pathogenic bacteria in digestive organs characterized by containing the peptide according to the present invention.

According to the colonization inhibitor according to the present invention, it is possible to inhibit the binding between the type IVb pili and the target cells of digestive organs since the inhibitor contains the peptide according to the present invention. As a result, it is possible to inhibit adhesion and colonization of type IVb pili-producing bacteria in digestive organs.

According to the peptide of the present invention and the colonization inhibitor containing the same, it is possible to inhibit adhesion and colonization of type IVb pili-producing bacteria in digestive organs.

BRIEF DESCRIPTION OF THE DRAWINGS

FIGS. 1 (a) and (b) are model diagrams for explaining a mechanism by which pathogenic bacteria having type IVb pili adhere to and colonize on cells constituting a digestive organ and the like.

FIGS. 2 (a) and (b) are model diagrams for explaining a mechanism by which a peptide according to an embodiment of the present invention inhibits adhesion and colonization thereof.

FIG. 3 is a model diagram showing a three-dimensional structure of CofA and CofB which are constituent components of CFA/III pilus.

FIG. 4 (a) is a view showing a configuration of a cof operon which is a group of genes constituting CFA/III, and FIG. 4 (b) is a view for explaining the formation of type IV pili consisting of CofA and CofB.

FIG. 5 (a) is a view showing a trimeric structure of CofB, and FIG. 5 (b) is a view showing a trimeric structure of Discoidin I.

FIGS. 6 (a) and (b) are views showing the binding between CofJ and CofB.

FIG. 7 is a model diagram showing a crystal structure of a complex in which $CofJ^{1-24}$ peptide and CofB are bound.

FIG. 8 is a view which shows homologous genes in each coding region coding for type IVb pili, showing cof operon, lng operon, Tcp operon and cfc operon.

FIG. 9 is a view which shows the amino acid sequences of N-terminal regions of CofJ, LngJ, CfcJ and TcpF.

FIGS. 10 (a) to (c) are model diagrams showing the results of structure analysis of CofB, and (a) shows its overall structure, (b) shows an enlarged view of the area enclosed by a square in (a) and (c) is a diagram showing the top side of (b).

FIG. 11 is a view showing the results of a pull-down assay for examining whether the $CofJ^{1-24}$-GCN4 inhibitory peptide can inhibit the binding between CofB and CofJ.

FIG. 12 is a view showing the results of a pull-down assay for examining whether the $CofJ^{1-24}$ peptide and CofJpepR can inhibit the binding between CofB and CofJ.

FIG. 13 is a graph showing the results of measurement of the ETEC adhesion inhibitory activity of the $CofJ^{1-24}$-GCN4 inhibitory peptide using Caco2 cells.

FIG. 14 is a views showing the results of a pull-down assay for examining whether the $CofJ^{4-16}$-GCN4 inhibitory peptide can inhibit the binding between CofB and CofJ.

FIG. 15 is a graph showing the results of measurement of the ETEC adhesion inhibitory activity of the $CofJ^{4-16}$-GCN4 inhibitory peptide using Caco2 cells.

DETAILED DESCRIPTION

Embodiments for carrying out the present invention will be described below. The following descriptions of preferred embodiments are merely substantially exemplary and are not intended to limit the present invention, its application methods or its uses.

The peptide according to the embodiment of the present invention is a peptide which can bind to pili, particularly to type IVb pili of pathogenic bacteria, thereby preventing the pathogenic bacteria from binding to receptors of target cells via the pili. The peptide according to this embodiment comprises a first domain that binds to type IVb pili, a second domain that is capable of multimerizing, and a linker sequence that connects them.

In the present embodiment, the pathogenic bacteria are pathogenic bacteria in particular having type IVb pili, for example, enterotoxigenic *Escherichia coli* (ETEC), cholera (*Vibrio cholerae*), *Citrobacter rodentium* and the like.

First, outlines of a mechanism of adhesion and colonization of pathogenic bacteria having type IVb pili such as ETEC to cells constituting a digestive organ and the like and a mechanism by which the peptide according to this embodiment inhibits adhesion and colonization thereof will be illustrated.

As shown in FIG. 1 (a), the above-mentioned ETEC and the like form pili constituted of major pilin as the major constituent subunit and a minor pilin slightly contained and situated at the tip of the major pilin, on the surface thereof. In particular, they form a multimer, for example, a homotrimer. ETEC and the like can not adhere to the target cells in digestive organs and the like only by the pili having such a configuration, and secretory proteins expressed by ETEC and the like are necessary for adhesion. In the minor pilin, a binding site of a secretory protein is present and the secretory protein binds to minor pilin, whereby the pilus can bind to receptors of the target cells through the secretory protein as shown in FIG. 1 (b). As a result, ETEC adheres to target cells, then, microcolonies and the like are formed, thereby colonization is made possible.

As described above, the peptide according to the present embodiment has a first domain that binds to type IVb pili, and as shown in FIG. 2, the first domain of the peptide binds to a secretory protein binding site in minor pilin of the pili, as a result, it is possible to inhibit the secretory protein from binding to the binding site. In particular, since the peptide according to the present embodiment has a second domain that promotes multimerization, particularly trimerization, the peptide forms a trimer and can bind to all binding sites of pili of the trimer as shown in FIG. 2 (b). By this means, it is possible to efficiently inhibit the binding of secretory proteins to pili, and as a result, it is possible to efficiently inhibit adhesion and colonization of pathogenic bacteria such as ETEC and the like to target cells.

These mechanisms will be described in more detail below.

(Mechanism of Formation of Type IVb Pilus)

Bacteria that produce type IVb pili such as ETEC and the like express colonization factors, which are responsible for the formation of pilus. As a colonization factor to form type IVb pili on bacteria, CFA/III (CS8) is known, and as other colonization factors having the gene structure and constituent proteins which are very similar to this, Longus (CS21) is known. Type IV pili are roughly classified to type IVa or IVb depending on the N-terminal sequence and overall size of the major pilin that is the main constituent subunit, and CFA/III (CS8) and Longus (CS21) belong to the type IVb.

Previous functional analysis studies have revealed that cof operon which is a gene group constituting the CFA/III is constituted of 14 kinds of gene groups including the gene cofA encoding major pilin, the gene cofB encoding minor pilin and the like (Taniguchi, T. et al. Infect. Immun. 2001, 69, 5864-5873). Furthermore, the present inventors have determined the steric conformation of CofA and revealed the structure of pili formed by CFA/III (Fukakusa, S. et al. Acta Cryst. 2012, D68, 1418-1429) (FIG. 3). Further, as shown in FIG. 3, three-dimensional structure determination using X-ray crystal structure analysis and analysis of the associated state in solution by ultracentrifugation analysis have revealed that the minor pilin CofB constituting the pili formed by CFA/III forms a strong homotrimeric structure in which the pilin-like domain at the N-terminal side and two domains rich 13 sheets at the central portion and the C-terminal side are entangled helically. In addition, it has also been clarified that the trimer structure is located at the tip of the type IVb pilus which is mainly composed of major pilin CofA and plays a role of promoting the initiation of pili formation, as shown in FIGS. 4 (a) and 4 (b) (Kawahara, K. et al. J. Mol. Biol. 2016, 428, 1209-1226).

The tips of the type IVb pili are bundled by a domain rich in β sheets existing on the C-terminal side of the minor pilin CofB, and as a result of search of analogous domains, it has been clarified that this domain has a type H lectin-like folded structure, as shown in FIG. 5 (a). As the type H lectin domain, Discoidin I (FIG. 5 (b)) and Discoidin II of Dictyostelium discoideum and Helix pomatia agglutinin (HPA) discovered from snail called apple snail are known, and in recent years, Sinularia lochmodes (SLL2) of *Symbiodinium* sp. is known (Lescar, J. et al. Glycobiology 2007, 17, 1077-1083; Kita, A. et al. Glycobiology 2015, 25, 1016-1023), in addition to the CFA/III pili held by ETEC, and all of them form a homotrimer. At the molecular boundary of the trimer, there are three equivalently preserved sugar chain binding sites. It has been confirmed that N-acetyl-D-galactosamine (GalNac) binds at the binding site in the case of Discoidin I, Discoidin II, HPA and SLL2. All of them are involved in cell adhesion and self-aggregation, by binding to sugar chains. Recognition of sugar chains by lectin domains has also been confirmed in type I pili.

(Mechanism of Adhesion and Colonization of ETEC)

Schematic mechanism of adhesion and colonization of ETEC to the target cell is as described above with reference to FIG. 1, and the mechanism of adhesion and colonization of ETEC to the target cells will be illustrated more in detail below.

Since the CofB has the lectin domain described above, the expression of the adhesion ability to the target cells is assumed to occur by the domain, but it has been clarified from the results of the cell assay described in detail in the examples below that the CFA/III strain of *E. coli* does not exert the adhesion ability to Caco2 cells only by type IVb pili produced on the surface and expression of the secretory protein CofJ encoded likewise by the cof operon is essential. This is a result which was clarified by the fact that the CofJ-deficient strain of ETEC prepared by the present inventors does not show adhesion ability despite having pili forming ability. From this result, it is thought that CofJ intervenes between the pili and intestinal epithelial cells, thereby participating in adhesion to the intestinal tract and subsequent colonization.

It has been clarified from the results of ultracentrifugation analysis and the like that CofJ interacts with CofB which is a subunit located only at the pilus tip among pilus constituent subunits as shown in FIGS. 6 (a) and 6 (b), and furthermore, it has been shown from the results of the X-ray crystal structure analysis and the like that CofJ binds to one of three equivalent binding sites present in the CofB trimer at the N-terminal secondary structure-free regions (1 to 24).

At present, various subtypes have been reported in CofJ, and vaccines using CofJ are difficult to develop since mutations tend to occur in particular on the surface of the globular domain of CofJ. It has also been reported that CofA, which is the main constituent subunit of pili, also undergoes a lot of mutations on the surface of pili (Njoroge, S M et al. FEMS Pathogens and Diseases 2015, 73, 1-4). On the other hand, amino acids in the interaction site between CofJ and CofB were also found to be highly conserved. This suggests that ETEC colonization can be inhibited by inhibiting the interaction between CofJ and CofB, and the peptide according to the present invention was found based on this idea.

(Constitution of Peptide)

As described above, the peptide according to the present embodiment comprises a first domain that binds specifically to minor pilin of type IVb pili, a second domain capable of multimerizing, and a linker sequence that connects them.

Specifically, the first domain contains an amino acid sequence capable of binding to the binding site of the secretory protein in minor pilin of the pilus. It is preferable that it has for example an amino acid sequence (SPSSSEG-GAFTVNMPKTSTVDDIR: SEQ ID NO: 1) in the N-terminal secondary structure-free regions (1 to 24-th) in CofJ capable of binding to CofB and homology with the sequence of SEQ ID NO: 1 is preferably at least 70%, more preferably 80% or more, further preferably 90% or more, particularly preferably 95% or more.

Further, in the crystal structure of a complex in which CofB and the N-terminal secondary structure-free regions in CofJ (CofJ$^{1-24}$) are bound, CofB, as shown in FIG. 7, recognizes particularly from the fifth serine to the fifteenth proline of the CofJ$^{1-24}$ peptide, and, among which, the tenth phenylalanine is pierced deep into the hydrophobic pocket of CofB. Thus, the first domain can achieve binding to CofB by containing at least an amino acid sequence (SEGGAFT-VNMP: SEQ ID NO: 5).

In addition, the second domain contains a sequence that promotes multimerization, particularly trimerization, so that it can bind to all of the binding sites at the tip of type IV pili showing the trimeric structure. For example, as a peptide enabling trimerization, a peptide modified to enable trimerization of GCN4 leucine zipper (RMKQIEDKIEEILSKI-YHIENEIARIKKLI: SEQ ID NO: 6) (Harbury et al. Nature 1994, 371, 80-83), a collagen-like model peptide composed of repeating sequences of (Pro-Pro-Gly)n (SEQ ID NO: 7) or (Pro-Hyp-Gly)n (SEQ ID NO: 8) in which n=4 to 10, and the like, can be used. Here, Hyp is 4 (R)-hydroxyproline.

The linker sequence is not particularly limited as long as it functions as a linker, and for example, TSGGG (SEQ ID NO: 9) and the like can be used.

In the above description, the type IVb pili formed mainly by the colonization factor CFA/III has been described, however, type IVb pili formed by Longus expressed by ETEC, Tcp expressed by *Vibrio cholerae*, Cfc expressed by *C. rodentium* and the like as other colonization factors are known to have high similarities to pili by the CFA/III (Mundy, R. et al. Mol. Microbiol. 2003, 48, 795-809). LngA (L Ongus), TcpA (Tcp) and CfcA (Cfc) have been identified as those corresponding to the major pilin CofA, and the pilin-specific hydrophobic regions at their N-terminal side have a high sequence homology of 70 to 75%. FIG. 8 shows lng operon expressing LngA or the like, tcp operon expressing TcpA or the like, and cfc operon expressing CfcA or like, together with the cof operon expressing CofA or the like. As shown in FIG. 8, not only CofA, LngA, TcpA and CfcA but also many homologous genes are present.

Also, LngB (Longus), TcpB (Tcp) and CfcB (Cfc) corresponding to the minor pilin CofB likewise mutually have similarities. In addition to these, the N-terminal sequences of LngJ (Longus), TcpF (Tcp) and CfcJ (Cfc) corresponding to the secretory protein CofJ also have similarities. FIG. 9 shows the amino acid sequences of their N-terminal regions. In FIG. 9, the arrow shows the 10-th phenylalanine of CofJ involved strongly in the binding to CofB described above, and the underline shows a sequence portion which would not form a secondary structure. The underlined portion corresponds to the sequences of SEQ ID NOs: 1 to 4 related to the peptide of the present embodiment, and this sequence is a sequence of a portion not forming a secondary structure as described above, that is, it is a sequence favorable for the binding to minor pilin.

The peptide of the present embodiment may be modified to prevent decomposition of the peptide and the like.

The method of preparing the peptide according to the present embodiment is not particularly limited, and a method that is generally used for peptide synthesis can be used, and for example, a genetic engineering method or a chemical method using organic synthesis can be used, more specifically, methods shown in the following examples can be used.

Another embodiment of the present invention is a colonization inhibitor comprising the above-described peptide of the present invention for inhibiting adhesion and colonization of bacteria producing type IVb pili to target cells in digestive organs and the like. The colonization inhibitor according to this embodiment may contain additives such as a stabilizer, a buffer, a diluent, an excipient and the like in addition to the above-mentioned peptide. In addition, the colonization inhibitor according to this embodiment is preferably in a dosage form capable of oral administration, and is preferably, for example, a tablet, a capsule, a pill or the like, but is not limited thereto. In addition, the colonization inhibitor according to the present embodiment may be subjected to coating treatments such as enteric coating using cellulose acetate phthalate (CAP), hypromellose phthalate (HPMCP), acrylic acid type polymer and the like, sustained-release coating using ethyl cellulose and the like, but the treatment is not limited to them.

EXAMPLES

The effect of the peptide according to the present invention on the colonization ability by CFA/III pili of ETEC will be explained below as typical examples of the present invention.

(Example 1) Experiment of Adhesion of *Escherichia coli* CFA/III Producing Strain to Caco2 Cells From the reports so far, not only the CFA/III producing wild type ETEC 31-10 strain (ETEC 1373 strain) cultured with CFA agar but also the strain (HB101 cof) obtained by introducing the plasmid pTT240 containing the cof operon into *E. coli* HB101 strain (Nippon Gene) have been reported to have type IVb pili forming ability like the wild type under the same culture conditions and adhere to Caco2 cells (Honda, T. et al. Infect. Immun 1989, 57, 3452-3457; Taniguchi, T. et al. Infect. Immun 2001, 69, 5864-5873). Here, the plasmid pTT240 containing the cof operon was prepared by the following procedure. First, as a result of base sequence analysis of the cof gene cluster, the presence of the cleavage site of the restriction enzyme KpnI upstream of the promoter sequence of the cof gene and the cleavage site of the restriction enzyme StuI downstream of the cofJ gene which is the last gene of the cof gene cluster became clear, hence the plasmid pSH1134 containing the cof gene cluster was cleaved with the restriction enzyme StuI, then, phosphorylated KpnI linker (Takara Shuzo) was ligated and cleaved with the restriction enzyme KpnI. The resultant 13.8 kb fragment was subjected to electrophoresis on a 0.8% agarose gel, purified, then, ligated to the plasmid pMW 119 (Nippon Gene) treated with the restriction enzyme KpnI. The obtained plasmid was named pTT240. In addition, Caco2 cells are considered to be model cells for colonization of ETEC to small intestinal epithelial cells (Darfeuille-Michaud, A. et al. Infect. Immun 1990, 58, 893-902). Therefore, adhesion experiments were conducted using HB 101 cof and Caco2 cells as follows.

First, Caco2 cells were dispersed using Dulbecco's Modified Eagle's Medium (DMEM) containing 50 µg/mL gentamicin and 10% fetal bovine serum, the cell concentration was measured using a blood cell counting chamber and diluted to $3.0 \times 10^5$ cells/mL. Dilution liquid was added to a 6-well plate each in an amount of 500 µL, and culture was performed by allowing the plate to stand still in a $CO_2$ incubator at 5% $CO_2$ and 37° C. for 48 hours. The cultured Caco2 cells were washed with PBS twice. After washing, DMEM containing 100 μg/mL ampicillin and 1% D-mannose was filtrated by passing through a 0.22 μm filter, then, the solution was added each in an amount of 500 μL to each well.

Next, a small amount of the glycerol stock of HB101 cof was scraped off and added to LB medium containing 100 μg/mL ampicillin, and shaking culture was carried out overnight at 25° C. The culture liquid was suitably diluted and $OD_{660}$ of the culture liquid was calculated using a turbidimeter. The culture liquid was serially diluted and CFU (colony forming unit) was measured. From the measured CFU, the concentration (cells/mL) of HB101 cof at $OD_{660}=1.0$ was calculated. This calculated value was used to determine the concentration of HB101 cof later.

Apart from the above culture, a small amount of the glycerol stock of HB101 cof was scraped off and added to LB medium containing 100 μg/mL ampicillin, and shaking culture was carried out overnight at 25° C. The bacterium culture liquid was diluted 10 times with LB medium containing 100 μg/mL ampicillin and transferred in an amount of 500 μL to a CFA agar plate (1% Casamino Acid, 0.15% yeast extract, 0.005% $MgSO_4$, 0.0005% $MnCl_2$, 2% agarose) and culture was performed by allowing the plate to stand still at 37° C. for 24 hours. 3 mL of PBS was added to the agar medium after culture, and the suspension was suspended with a spreading stick, then, recovered. The recovered culture liquid was diluted 100 times and $OD_{660}$ was measured. $OD_{660}$ of the culture liquid before dilution was calculated from the measured $OD_{660}$, and the *E. coli* concentration (cells/mL) was calculated based on the concentration (cells/mL) of HB101 cof at $OD_{660}=1.0$ described above. HB101 cof was diluted with PBS to $1.0 \times 10^9$ cells/mL to prepare a sample for colonization assay.

The prepared sample was added in an amount of 50 μL to Caco2 cells in the 6-well plate, and the plate was allowed to stand still in a $CO_2$ incubator at 5% $CO_2$ and 37° C. for 3 hours. Three hours later, after washing three times with PBS, 500 μL of PBS containing 0.1% Triton X-100 was added, and after standing still for 5 minutes, it was recovered. The recovered solution was serially diluted and CFU was measured. From measured CFU, the number of bacteria colonized on Caco2 cells was calculated. The recovery rate (%) was calculated by dividing the number of bacteria that had been colonized by the number of bacteria added to Caco2 cells ($5.0 \times 10^7$ cells) and multiplying by 100. As a result, it was 16.9% and the adhesion ability in this experimental system was confirmed.

(Example 2) Experiment of Adhesion of CofB-Deficient Strain and CofJ-Deficient Strain to Caco2 Cells In the above Example 1, it was confirmed that HB101 cof was able to adhere to Caco2 cells, hence, CofB-deficient strain and CofJ-deficient strain were then prepared, and the functions of CofB and CofJ were examined. The method will be described below.

First, a cofJ gene-deficient strain (HB101-cof-ΔcofJ) was prepared based on plasmid pTT240. Paying attention to the presence of the cleavage site of the restriction enzyme NcoI at two places in the ORF region of the cofJ gene, the strain was cleaved by incubating at 37° C. for 1 hour with NcoI, followed by purification. The plasmid obtained by ligating the purified cleavage product was designated as CofJ-deficient plasmid pcof-ΔcofJ. A strain obtained by transforming *Escherichia coli* strain HB101 with pcof-ΔcofJ was designated as CofJ-deficient strain HB101-cof-ΔcofJ.

In order to complement the cofJ gene to the cofJ-deficient strain in trans configuration, it was decided to incorporate the cofJ gene into plasmid vector pACYC184. Paying attention to the presence of the restriction enzyme sites of SalI upstream and HindIII downstream of the cofJ gene in the plasmid pTT240, after the restriction enzyme treatment, the end of the cleavage product was blunted and the product was purified. The plasmid obtained by ligating the purified cleavage product with EcoRV-treated plasmid vector pACYC184 (NIPPON GENE) was designated as cofJ complemented plasmid pcofJ. A strain obtained by transforming *Escherichia coli* strain HB101 with pcof-ΔcofJ and pcofJ was designated as CofJ complemented strain HB101-cof-ΔcofJ+pcofJ.

The CofB-deficient strain HB101-cof-ΔcofB and the CofB complemented strain HB101-cof-ΔcofB+pcofB were fabricated according to the cited literature (Kawahara, K, et al. J. Mol. Biol, 2016, 428, 1209-1226). Experiments of adhesion of the CofJ-deficient strain HB101-cof-ΔcofJ, the CofJ complemented strain HB101-cof-ΔcofJ+PcofJ, the CofB-deficient strain HB101-cof-ΔcofB and the CofB complemented strain HB101-cof-ΔcofB+pcofB were conducted in the same manner as in Example 1.

As a result of the experiment, the recovery rate was 0.30% for the CofJ-deficient strain HB101-cof-ΔcofJ, 2.9% for the CofJ complemented strain HB101-cof-ΔcofJ+pcofJ, 0.79% for the CofB-deficient strain HB101-cof-ΔcofB and 2.9% for the CofB complemented strain HB101-cof-ΔcofB+pcofB.

That is, the CofJ-deficient strain HB101-cof-ΔcofJ adhered to Caco2 cells only 0.018 times and the CofB-deficient strain HB101-cof-ΔcofB adhered only 0.047 times, as compared with HB101 cof. In addition, although the CofJ complemented strain HB101-cof-ΔcofJ+pcofJ and the CofB complemented strain HB101-cof-ΔcofB+pcofB did not have the colonization ability as much as HB101 cof, recovery of the colonization ability was observed as compared with each deficient strain. Therefore, it is recognized that CofB and CofJ are involved in adhesion to Caco2 cells by HB101 cof.

(Example 3) Analysis of Interaction Between CofJ and Pilus Subunit

Next, the interaction between a secretory protein CofJ and pilus constituent subunits CofA and CofB was analyzed.

To analyze the interaction between CofJ and pilus constituent subunits CofA and CofB, constructs (ΔN28-CofA, ΔN28-CofB) excluding the hydrophobic region (1 to 28 residues) at the N terminal of CofA and CofB were designed for improvement of solubility, and expression and purification thereof were conducted. The expression and purification methods were carried out according to past papers (Fukakusa, S, et al. Acta Cryst. 2012, D68, 1418-1429; Kawahara, K, et al. J. Mol. Biol, 2016, 428, 1209-1226).

Expression and purification of CofJ were performed by the following procedure. Amplification by PCR was performed from plasmid pTT240 using forward primer: 5'-GCGCCCGGGTCGCCATCCTCTTCAGAAGG-3' (SEQ ID NO: 10) and reverse primer: 5'-CAAGAATTCT-TATTAATCAAGGCCACAAGCTTC-3' (SEQ ID NO: 11). After treatment with the restriction enzymes SmaI and EcoRI, a plasmid ligated to the pET48b vector (Merck Biosciences) treated in the same manner was used as the CofJ expression plasmid. A strain obtained by transforming *E. coli* strain Shuffle T7 Express lysY Competent *E. coli*

(New England Biolabs) using the CofJ expression plasmid was shaking-cultured at 37° C. with LB medium containing 35 µg/mL kanamycin as preculture. All of the preculture liquid was added to the main culture liquid and cultured at 37° C. until the $OD_{660}$ reached 0.60. Expression induction was carried out by adding 0.2 mM IPTG, and shaking culture was carried out at 20° C. for 18 hours. The microbial body was recovered by centrifugation at 4000 G and 4° C. for 7 min and suspended in Lysis buffer (50 mM Tris-HCl, 1 M NaCl, pH 8.0) on ice, and lysozyme in a final concentration of 0.2 mg/mL and Triton-X 100 in a final concentration of 0.2% were added and the mixture was allowed to stand still for 15 minutes. The microbial body was disrupted by ultrasound (10 seconds, 50 seconds rest, 15 cycles), and the supernatant containing the soluble protein was recovered by centrifugation at 24000 G and 4° C. for 1 hour. The resulting supernatant was added to a HiTrap chelating column (GE Healthcare Biosciences) which bound $Ni^{2+}$ and equilibrated with the above lysis buffer. After washing with the above-described lysis buffer containing 15 mM imidazole added, CofJ with the Histag was eluted by 15 to 500 mM imidazole gradient. 30 units of Turbo 3C protease (Accelagen) was added to the eluted fraction and the fusion tag was cleaved at 10° C. while dialyzing against 50 mM Tris-HCl, 150 mM NaCl, pH 8.0, 15 mM Imidazole. The fusion tag-cleaved CofJ was allowed to pass through an equilibrated Ni column, to cause separation from the tag. The separated CofJ was subjected to final purification using a gel filtration column Superdex 75 (GE Healthcare Biosciences) equilibrated with 20 mM Tris-HCl, 150 mM NaCl, pH 8.0.

Expression of ΔN24-CofJ not having 24 residues on the N-terminal side of CofJ was carried out as follows. After amplification by inverse PCR using forward primer: 5'-GGTTGCCCAACTTTGGAAAC-3' (SEQ ID NO: 12) and reverse primer: 5'-ACCCAGACCCGGGTCCCT-GAAAGAG-3' (SEQ ID NO: 13) based on the vector for CofJ expression, blunting with the restriction enzyme SmaI was conducted, then, ligation was performed to obtain a plasmid designated as CofJΔ24 expression plasmid. Expression and purification of CofJΔ24 were performed in the same manner as for CofJ.

Interaction analysis was performed using CofB, CofJ and ΔN24-CofJ prepared by the above methods. An isothermal titration calorimeter Microcal iTC 200 (manufactured by GE Healthcare) was used for analysis of the interaction between the secretory protein CofJ and ΔN28-CofB. A 0.59 mM CofJ solution was charged in a titration syringe and a 28.5 µM (in terms of trimer) ΔN28-CofB solution was charged in a measuring cell, respectively, and the interaction of them was evaluated by directly observing heat changes that occur upon dropping the CofJ solution into the ΔN28-CofB solution. Titration conditions were such that the initial dropping amount was 1 µL, the dropping amount at the second and subsequent times was 2 µL, and dropping was performed 20 times in total every 120 seconds. The measurement temperature was 25° C., and the solvent was 20 mM Tris-HCl (pH 8.0), 150 mM NaCl. An exothermic change was observed by dropping the CofJ solution, which converged to the same level as the heat of dilution as the titration progressed. As a result of analysis of the obtained data using an analysis software Origin (Microcal), binding of CofJ and ΔN28-CofB was observed. The dissociation constant Kd value of both was 0.2 µM.

Similarly, an isothermal titration calorimeter Microcal iTC 200 (manufactured by GE Healthcare) was used for analysis of the interaction between CofJ and ΔN28-CofA. A 0.59 mM CofJ solution was charged in a titration syringe and a 28.5 µM (in terms of trimer) ΔN28-CofA solution was charged in a measuring cell, respectively, and the interaction of them was evaluated by directly observing heat changes that occur upon dropping the CofJ solution into the ΔN28-CofA solution. The titration conditions and solvent conditions were the same as in the analysis of the interaction between the secretory protein CofJ and ΔN28-CofB. No change in caloric value due to dropping of the CofJ solution was observed. From this, it was shown that CofJ and ΔN28-CofA do not bind.

Next, in order to investigate the contribution to binding to pili in the N-terminal region (1 to 24) of the secretory protein CofJ, analysis of the interaction between ΔN24-CofJ and ΔN28-CofB was carried out using an isothermal titration calorimeter Microcal iTC 200 (manufactured by GE Healthcare). A 0.59 mM ΔN24-CofJ solution was charged in a titration syringe and a 28.5 µM (in terms of trimer) ΔN28-CofB solution was charged in a measuring cell, respectively, and the interaction of them was evaluated by directly observing heat changes that occur upon dropping the ΔN24-CofJ solution into the ΔN28-CofB solution. No change in caloric value due to dropping of the ΔN24-CofJ solution was observed. From this, it was shown that ΔN24-CofJ and ΔN28-CofB do not bind.

Furthermore, in order to investigate the contribution to binding to pili in the N-terminal region (1 to 24) of the secretory protein CofJ, analysis of the interaction between a synthetic peptide consisting of 24 amino acid residues at the N terminal of CofJ ($CofJ^{1-24}$ peptide) purchased from Scrum Co., Ltd. and ΔN28-CofB was carried out using an isothermal titration calorimeter Microcal iTC200 (manufactured by GE Healthcare) in the same manner as described above. A 2 mM $CofJ^{1-24}$ peptide solution was charged in a titration syringe and a 33.9 µM (in terms of trimer) ΔN28-CofB solution was charged in a measuring cell, respectively, and the interaction of them was evaluated by directly observing heat changes that occur upon dropping the $CofJ^{1-24}$ peptide solution into the ΔN28-CofB solution. An exothermic change was observed by dropping the $CofJ^{1-24}$ peptide solution, which converged to the same level as the heat of dilution as the titration progressed. As a result of analysis of the obtained data using an analysis software Origin, binding of the $CofJ^{1-24}$ peptide and ΔN28-CofB was observed. The dissociation constant Kd value of both was 4 µM.

Next, in order to investigate the binding specificity of the $CofJ^{1-24}$ peptide, analysis of the interaction between a synthetic random peptide (CofJpepR) purchased from Scrum Co., Ltd. and ΔN28-CofB was carried out using an isothermal titration calorimeter Microcal iTC 200 (manufactured by GE Healthcare). A 2 mM random peptide solution was charged in a titration syringe and a 28.5 µM (in terms of trimer) ΔN28-CofB solution was charged in a measuring cell, respectively, and the interaction of them was evaluated by directly observing heat changes that occur upon dropping the ΔN24-CofJ solution into the ΔN28-CofB solution. No change in caloric value due to dropping of the random peptide solution was observed. From this, it was shown that the random peptide and ΔN28-CofB do not bind.

From the above, it is suggested that CofA and CofJ do not bind, but CofB and CofJ bind to each other, and particularly 1 to 24 amino acid residues at the N terminal of CofJ are involved.

(Example 4) Determination of Association Ratio of CofJ to ΔN28-CofB by Ultracentrifugation Analysis Next, the association ratio of CofJ to ΔN28-CofB was examined. For the determination of their association ratio, an analytical ultracentrifuge Optima XL-I (manufactured by Beckman Coulter) was used. Quartz was selected for the window of the measurement cell, and 6-hole center piece made of Charcoal Epon having a cell length of 1.2 cm was used as the center piece. The measurement temperature was 20° C., and the solvent was 20 mM Tris-HCl (pH 8.0), 150 mM NaCl. The rotor rotation speed was set to 5000, 8000, 10000 rpm, and the concentration gradient in the cell was monitored by an UV detector every 2 hours after reaching the set rotation speed at each rotation number. At the time when the rmsd value of the absorbance observed for each scan became 0.01 or less, the sedimentation equilibrium was established, and after equilibrium was confirmed, the concentration gradient at sedimentation equilibrium was evaluated at 297 nm. The number of integrations was set to 4 times. It was confirmed that one molecule of CofJ and one molecule of trimer ΔN28-CofB were associated, from the concentration gradient obtained as described above and the apparent molecular weight calculated based on this.

(Example 5) Determination of Structure of Complex of $CofJ^{1-24}$ Peptide and CofB Next, in order to determine the structure of the complex consisting of the $CofJ^{1-24}$ peptide and CofB described above, attempts were made to prepare crystals of the complex.

For this purpose, firstly, the $CofJ^{1-24}$ peptide obtained by peptide synthesis was mixed with ΔN28-CofB so as to be doubled in the substance amount ratio, to obtain a crystallized sample. Initial screening was carried out at 20° C. by a sitting drop vapor diffusion method using a screening kit Wizard Screen I, II (Emerald Biosystems). Each drop, 1 μL of the above-described mixed peptide (ΔN28-CofB/$CofJ^{1-24}$ peptide) prepared so that the concentration of CofB was 10, 5, 2.5 mg/mL and 1 μL of the crystallization solution were mixed and allowed to stand still. As a result of screening, initial crystals were obtained under the conditions of Wizard II-39 (100 mM CAPS, pH 10.5, 20% PEG 8000, 200 mM NaCl). After optimizing the conditions, a drop of 3 to 4 μL was formed by mixing equal amounts of ΔN28-CofB/$CofJ^{1-24}$ peptide having a concentration of 5 mg/mL and a crystallization solution using 40 μL of the crystallization solution as a reservoir, and it was allowed to stand still at 20° C. for 3 days, thus, acicular crystals could be obtained.

For the resultant ΔN28-CofB/$CofJ^{1-24}$ peptide complex crystals, diffraction measurements were carried out on the large synchrotron radiation facility SPring-8 BL26B1. After recovering the complex crystal from the drop with nylon loop, quick freezing in a nitrogen stream of −173° C. was performed, and the diffraction data were recovered. Diffraction images from the complex crystals showed a diffraction ability of the highest resolution of 3.85 Å. Intensity integration and scaling processing were performed using program HKL2000. The complex crystals belonged to the space group P65, and the lattice constants were a=157.76 Å, b=157.76 Å, c=118.53 Å, α=β=90.0° and γ=120.0°. Determination of the initial phase was performed by a molecular replacement method using a program Phaser. The coordinate data of ΔN28-CofB (PDBID: 5AX6) was used as the coordinate data of the initial search model in applying the molecular replacement, and considering the existence of a linker between domain 1 and domain 2 with high mobility, those decomposed into two fragments: a domain 1 fragment and other fragment (trimer fragment composed of domains 2 to 3) were adopted as the initial search model, and the solution of the initial phase by molecular replacement was obtained. As a result, one solution containing three domain 1 monomer fragments and one trimer fragment composed of domains 2 and 3 adopted as the initial search model was found. Fragments resulting from the molecular replacement method were connected by a molecular modeling support program Coot, then, refinement of the initial structure by a structure refinement program PHENIX.refine was performed, as a result, the electron density of the $CofJ^{1-24}$ peptide was observed at three places in the molecular boundary of the type H lectin domain of a ΔN28-CofB trimer, as shown in FIG. 10.

From these results, it was suggested that three CofJ peptides can bind in the type H lectin domain of a CofB trimer.

(Example 6) Design of GCN4 Fusion Type Inhibitory Peptide

Next, in order to prepare a trimeric peptide capable of binding to the type H lectin domain of each of the above-mentioned CofB trimers, GCN4 having a trimerizing domain was used, and attempts were made to create a peptide in which GCN and a CofJ peptide are bound via a linker.

Therefore, firstly, the expression plasmid of an inhibitory peptide (called $CofJ^{1-24}$-GCN4) in which the $CofJ^{1-24}$ peptide and GCN4 were fused using a linker (TSGGG) was constructed as follows. Oligonucleic acids were connected by a PCR reaction, to synthesize the $CofJ^{1-24}$-GCN4 gene. CJN-T-1, 6 (Table 1) were prepared to have a final concentration of 0.6 μM and CJN-T-2, 3, 4, 5 (Table 1) were prepared to have a final concentration of 0.03 μM, and 20 cycles of PCR were performed. The resultant amplified product was cleaved with restriction enzymes NdeI/XhoI, purified, and ligated to a pET30a vector (MERCK Biosciences) treated in the same manner, to obtain a plasmid. However, since $CofJ^{1-24}$-GCN4 was not expressed in this plasmid, it was decided to be expressed by a vector to which a GST tag was added at the N terminal. PCR was performed for 35 cycles using CJN-T-7,8 as a primer and the above-described plasmid as a template. The resultant amplified product was cleaved with the restriction enzymes BamHI/XhoI, purified, and ligated to a pGEX6P-1 vector (GE Healthcare Biosciences) treated in the same manner, to obtain a $CofJ^{1-24}$-GCN4 expression plasmid.

TABLE 1

| Primer | Primer base sequence |
|---|---|
| CJN-T-1 (SEQ ID NO: 14) | 5V-GTTCCACATATGAGCCCGTCTTCCAGCGAAGGTGGTGC TTTCACCGTTAAC-3' |
| CJN-T-2 (SEQ ID NO: 15) | 5'-GACCTCTACTGTTGACGATATCCGTACTAGTGGTGGCG GTCGTATGAAACAGATC-3' |
| CJN-T-3 (SEQ ID NO: 16) | 5'-GATCGAGGAAATCCTGTCCAAGATCTACCACATCGAAA ACGAGATCGCGC-3' |
| CJN-T-4 (SEQ ID NO: 17) | 5'-GGATATCGTCAACAGTAGAGGTCTTCGGCATGTTAACG GTGAAAGCACCACC-3' |
| CJN-T-5 (SEQ ID NO: 18) | 5'-CTTGGACAGGATTTCCTCGATCTTGTCTTCGATCTGTT TCATACGACCGCC-3' |

TABLE 1-continued

| Primer | Primer base sequence |
|---|---|
| CJN-T-6 (SEQ ID NO: 19) | 5'-CTAGCTCTCGAGTTAGATAAGCTTCTTGATACGCGCGA TCTCGTTTTCGATG-3' |
| CJN-T-7 (SEQ ID NO: 20) | 5'-GTTCCAGGATCCCCGTCTTCCAGCGAAGGTG-3' |
| CJN-T-8 (SEQ ID NO: 21) | 5'-GGTGCTCGAGTTAGATAAGCTTCTTG-3' |

Next, an *Escherichia coli* strain BL21 (DE3) (NIPPON GENE) was transformed using a plasmid for expressing CofJ$^{1-24}$-GCN4. Colonies were picked, added to LB medium containing 100 μg/mL ampicillin, and shaking-cultured overnight at 37° C. The next morning, the whole culture liquid was added to the main culture medium and scaled up and cultured with shaking at 37° C. When reaching OD$^{660}$=0.6, IPTG was added to a final concentration of 1 mM and shaking was carried out at 25° C. for 18 hours, to induce expression. The expression-induced microbial body was recovered by centrifugation at 4000 G and 4° C. for 7 minutes. The resultant microbial body was dissolved with a lysis buffer (20 mM Tris-HCl, 1 M NaCl, pH 8.0) on ice, then, lysozyme was added at 20 μg/mL and Triton X-100 was added at 0.2% and the sample was left for 15 minutes, then, the cycle of ultrasonic disruption for 15 seconds and break for 1 minute was repeated 15 times. The ultrasonic-disrupted solution was centrifuged at 20000 G and 4° C. for 1 hour, and the supernatant of centrifugation was filtered through a 0.8 μm filter. The filtered sample was applied to a GST column (Glutathione Sepharose 4 Fast Flow: GE Healthcare Biosciences) equilibrated with a lysis buffer. The GST column was washed with a lysis buffer, then, eluted with an elution buffer (20 mM Tris-HCl, 20 mM GSH, pH 8.0). The eluted sample was dialyzed with a dialysis buffer (20 mM Tris-HCl, pH8.0) while enzymatically treating with 30 units of Turbo 3C Protease (Accelagen), to cleave the GST tag and CofJ$^{1-24}$-GCN4. The sample after cleaving was applied to the GST column, to separate the GST tag and CofJ$^{1-24}$-GCN4. The recovered sample was applied to a Hitrap DEAE column (GE Healthcare Biosciences) equilibrated with a dialysis buffer, and elution was carried out by applying a gradient of NaCl concentration from 0 to 2 M. The resultant sample was applied to a Superdex 75 (26/60) column (GE Healthcare Biosciences) equilibrated with a gel filtration buffer (20 mM Tris-HCl, 150 mM NaCl, pH 8.0), to obtain a final purified product.

The resultant final purified product is constituted of 4 residues of the vector-derived sequence (GPLG), 24 residues derived from the CofJ N terminal region (CofJ$^{1-24}$ sequence) (SPSSSEGGAFTVNM PKTSTVDDIR: SEQ ID NO: 1), 5 residues of a linker sequence (TSGGG: SEQ ID NO: 9) and 30 residues of a GCN4 sequence (RMKQIED-KIEEILSKIYHIENEIARIKKLI) (SEQ ID NO: 6), from the N-terminal side. This is called CofJ$^{1-24}$-GCN4 inhibitory peptide.

(Example 7) Analysis of Interaction Between GCN4 Fusion Type Inhibitory Peptide and ΔN28-CofB by ITC In order to investigate the contribution to binding to pili of the CofJ$^{1-24}$-GCN4 inhibitory peptide obtained in Example 6, analysis of the interaction between the CofJ$^{1-24}$-GCN4 inhibitory peptide and ΔN28-CofB was carried out using an isothermal titration calorimeter Microcal iTC200 (manufactured by GE Healthcare). A 0.59 mM CofJ$^{1-24}$-GCN4 inhibitory peptide solution was charged in a titration syringe and a 28.5 μM (in terms of trimer) ΔN28-CofB solution was charged in a measuring cell, respectively, and the interaction of them was evaluated by directly observing heat changes that occur upon dropping the CofJ$^{1-24}$-GCN4 inhibitory peptide solution into the ΔN28-CofB solution. An exothermic change was observed by dropping the CofJ$^{1-24}$-GCN4 inhibitory peptide solution, which converged to the same level as the heat of dilution as the titration progressed. As a result of analysis of the obtained data using an analysis software Origin, binding of the CofJ$^{1-24}$-GCN4 inhibitory peptide and ΔN28-CofB was observed. The dissociation constant Kd value of both was 0.04 μM.

As a result of analysis, it was shown that the binding affinity between the CofJ$^{1-24}$-GCN4 inhibitory peptide and ΔN28-CofB was stronger about 5 times as compared with the binding affinity between CofJ and ΔN28-CofB and it was clarified that the GCN4 fusion type inhibitory peptide efficiently inhibits the interaction between CofJ and ΔN28-CofB.

(Example 8) Inhibition of CofB/CofJ Interaction by Inhibitory Peptide by Pull Down Assay To examine whether the CofJ$^{1-24}$-GCN4 inhibitory peptide is capable of inhibiting the binding of CofB and CofJ, it was confirmed in the in vitro experiment system by pull down assay using a Ni column. For experiments, ΔN28-CofB (Trx-His-ΔN28-CofB), CofJ, CofJ$^{1-24}$-GCN4, a CofJ$^{1-24}$ peptide and a peptide (CofJpepR) in which the amino acid sequence of the CofJ$^{1-24}$ peptide was randomized, with added thioredoxin tag (Trx) and His tag, were used. The sequence of CofJpepR is NPSGFDKSGSSTTRT-PAMSVIVDE (SEQ ID NO: 22).

Solutions mixed so that the concentration of Trx-His-ΔN28-CofB was 1 μM and the concentration of CofJ$^{1-24}$-GCN4 was (0, 0.5, 1.0, 2.0, 5.0, 10.0 μM) were allowed to stand still on ice overnight. Further, CofJ was mixed so that the final concentration became 1 μM, and the mixtures were allowed to stand still on ice for 1 hour, to obtain experiment samples. Each sample was applied to a Ni column equilibrated with 20 mM Tris-HCl, 150 mM NaCl, pH 8.0, and the column was washed with 20 mM Tris-HCl, 150 mM NaCl, 15 mM Imidazole, pH 8.0. Thereafter, elution was performed with 20 mM Tris-HCl, 150 mM NaCl, 300 mM Imidazole, pH 8.0, and the eluted fraction was confirmed by SDS-PAGE. The results are shown in FIG. 11. It was clarified that the binding of CofJ and Trx-His-ΔN28-CofB can be strongly inhibited by preliminarily mixing CofJ$^{1-24}$-GCN4 having the concentration not lower than that of CofJ with Trx-His-ΔN28-CofB, as shown in FIG. 11.

Also for the CofJ$^{1-24}$ peptide and CofJpepR, the inhibition ability thereof was investigated by the same method. Specifically, solutions mixed so that the concentration of Trx-His-ΔN28-CofB was 1 μM and the concentration of the CofJ$^{1-24}$ peptide and CofJpepR was 1000 μM were allowed to stand still on ice overnight. Further, CofJ was mixed so that the final concentration became 1 μM, and the mixtures were allowed to stand still on ice for 1 hour, to obtain experiment samples. The pull down assay was performed in the same manner as described above. The results are shown in FIG. 12. It was clarified that even if the CofJ$^{1-24}$ peptide is previously added with the concentration 1000 times of that of CofJ, the binding of CofJ and Trx-His-ΔN28-CofB can be hardly inhibited, as shown in FIG. 12. In addition, it was clarified that the binding can not be inhibited at all with CofJpepR. From this, it is considered that CofJ$^{1-24}$-GCN4 can inhibit the binding between CofB and CofJ by strongly binding with CofB by trimerizing.

(Example 9) Evaluation of ETEC Adhesion Inhibitory Activity of Inhibitory Peptide Using Caco2 Cells The colonization experiment was conducted in the same manner as in Example 1 and Example 2. In the experiment, mixtures were prepared so that the concentration of CofJ$^{1-24}$-GCN4 was 0, 10, 100, 1000 μg/mL and the concentration of HB101 cof was 1.0×10$^9$ cells/mL, then, the mixtures were allowed to stand still at 25° C. for 1 hour, and each 50 μL of the mixtures were added to 500 μL medium so that the concentration of CofJ$^{1-24}$-GCN4 was 0, 1, 10, 100 μg/mL and the concentration of HB101 cof was 1.0×10$^8$ cells/mL. The results are shown in FIG. 13. As shown in FIG. 13, the recovery rate was 14.7% for 0 μg/mL CofJ$^{1-24}$-GCN4, 14.0% for 1 μg/mL CofJ$^{1-24}$-GCN4, 11.5% for 10 μg/mL CofJ$^{1-24}$-GCN4 and 2.6% for 100 μg/mL CofJ$^{1-24}$-GCN4.

It was clarified from the results that CofJ$^{1-24}$-GCN4 inhibits colonization of HB101 cof to Caco2 cells in concentration-dependent manner.

(Example 10) Analysis of Interaction Between CofJ$^{4-16}$ Peptide and ΔN28-CofB by ITC It was hitherto shown that the CofJ$^{1-24}$ peptide inhibits the CofB/CofJ interactions, thereby inhibiting adhesion of ETEC to intestinal tissue. It is supposed from the crystal structure of the CofJ$^{1-24}$ peptide/ΔN28-CofB complex that a part of the CofJ$^{1-24}$ peptide, specifically, the fifth serine to the fifteenth proline are particularly involved in the interaction of both as shown in FIG. 7, as described above. Then, it was investigated whether a CofJ$^{4-16}$ peptide (SEQ ID NO: 23) composed of 4-th to 16-th amino acid sequences of the CofJ$^{1-24}$ peptide, containing a portion that is considered especially important in the CofJ$^{1-24}$ peptide, can exert the equivalent effect to the CofJ$^{1-24}$ peptide.

First, in order to investigate the contribution to binding to pili of the CofJ$^{4-16}$ peptide, analysis of the interaction between a CofJ$^{4-16}$ synthetic peptide (purchased from Scrum Co., Ltd.) and ΔN28-CofB was carried out using an isothermal titration calorimeter Microcal iTC 200 (manufactured by GE Healthcare) in the same manner as the experiment conducted in Example 3. Specifically, a 2 mM CofJ$^{4-16}$ peptide solution was charged in a titration syringe and a 33.9 μM (in terms of trimer) ΔN28-CofB solution was charged in a measuring cell, respectively, and the interaction of them was evaluated by directly observing heat changes that occur upon dropping the CofJ$^{4-16}$ peptide solution into the ΔN28-CofB solution. An exothermic change was observed by dropping the CofJ$^{4-16}$ peptide solution, which converged to the same level as the heat of dilution as the titration progressed. As a result of analysis of the obtained data using an analysis software Origin, binding of the CofJ$^{4-16}$ peptide and ΔN28-CofB was observed. The dissociation constant Kd value of both was 4 μM.

From the above, it was suggested that the CofJ$^{4-16}$ peptide can bind to CofB, like the CofJ$^{1-24}$ peptide.

(Example 11) Design of CofJ$^{4-16}$-GCN4 Peptide

Then, to make a trimer peptide also for CofJ$^{4-16}$, attempts were made to prepare a CofJ$^{4-16}$-GCN4 peptide using GCN4 having a trimerizing domain, and a linker, in the same manner as in Example 6.

The expression plasmid of an inhibitory peptide (referred to as CofJ$^{4-16}$-GCN4) in which a CofJ$^{4-16}$ peptide was fused to GCN4 using a linker (TSGGG) was constructed as follows. The sites of the restriction enzymes BamHI and SpeI which had been previously incorporated at both ends of the CofJ$^{1-24}$ peptide sequence in the CofJ$^{4-16}$-GCN4 expression plasmid were cleaved using both restriction enzymes, then, purified. By mixing and annealing the oligonucleotide 1: 5'-GATCCAGCGAAGGTGGTGCTTTCACCGT-TAACATGCCGAAGA-3' (SEQ ID NO: 24) and the oligonucleotide 2: 5'-CTAGTCTTCGGCATGTTAACGGT-GAAAGCACCACCTTCGCTG-3' (SEQ ID NO: 25) containing the sequence of Coif, double stranded DNA was prepared, which was then ligated to a purified vector, to obtain a CofJ$^{4-16}$-GCN4 expression plasmid.

Next, an *Escherichia coli* strain BL21 (DE3) (NIPPON GENE) was transformed with a plasmid for expressing CofJ$^{4-16}$-GCN4. Colonies were picked, added to LB medium containing 100 μg/mL ampicillin, and shaking-cultured overnight at 37° C. The next morning, the whole culture liquid was added to the main culture medium and scaled up and cultured with shaking at 37° C. When reached OD$_{660}$=0.6, IPTG was added to a final concentration of 1 mM and shaking was carried out at 25° C. for 18 hours, to induce expression. The expression-induced microbial body was recovered by centrifugation at 4000 G and 4° C. for 7 minutes. The resultant microbial body was dissolved in a lysis buffer (20 mM Tris-HCl, 1 M NaCl, pH 8.0) on ice, then, lysozyme was added at 20 μg/mL and Triton X-100 was added at 0.2% and the sample was left for 15 minutes, then, the cycle of ultrasonic disruption for 15 seconds and break for 1 minute was repeated 15 times. The ultrasonic-disrupted solution was centrifuged at 20000 G and 4° C. for 1 hour, and the supernatant of centrifugation was filtered through a 0.8 μm filter. The filtered sample was applied to a GST column (Glutathione Sepharose 4 Fast Flow: GE Healthcare Biosciences) equilibrated with a lysis buffer. The GST column was washed with a lysis buffer, then, eluted with an elution buffer (20 mM Tris-HCl, 20 mM GSH, pH8.0). The eluted sample was dialyzed with a dialysis buffer (20 mM Tris-HCl, pH8.0) while enzymatically treating with 30 units of Turbo 3C Protease (Accelagen), to cleave the GST tag and CofJ$^{4-16}$-GCN4. The sample after cleaving was applied to the GST column, to separate the GST tag and CofJ$^{4-16}$-GCN4. The recovered sample was applied to a Hitrap DEAE column (GE Healthcare Biosciences) equilibrated with a dialysis buffer, and the fraction not bound to the column was recovered. The resultant sample was applied to a Superdex 75 (26/60) column (GE Healthcare Biosciences) equilibrated with a gel filtration buffer (20 mM Tris-HCl, 150 mM NaCl, pH 8.0), to obtain a final purified product.

The resultant final purified product is constituted of 4 residues of the vector-derived sequence (GPLG), 13 residues derived from the CofJ N terminal region (SSEGGAFT-VNMPK: SEQ ID NO: 23), 5 residues of a linker sequence (TSGGG: SEQ ID NO: 9) and 30 residues of a GCN4 sequence (RMKQIEDKIEEILSKIYHIENEIARIKKLI:

SEQ ID NO: 6), from the N-terminal side. This is called CofJ$^{4-16}$-GCN4 inhibitory peptide.

(Example 12) Analysis of Interaction Between CofJ$^{4-16}$-GCN4 Inhibitory Peptide and ΔN28-CofB by ITC In order to investigate the contribution to binding to pili of the CofJ$^{4-16}$-GCN4 inhibitory peptide obtained in Example 11, analysis of the interaction between the CofJ$^{4-16}$-GCN4 inhibitory peptide and ΔN28-CofB was carried out using an isothermal titration calorimeter Microcal iTC200 (manufactured by GE Healthcare). A 0.59 mM CofJ$^{4-16}$-GCN4 inhibitory peptide solution was charged in a titration syringe and a 28.5 μM (in terms of trimer) ΔN28-CofB solution was charged in a measuring cell, respectively, and the interaction of them was evaluated by directly observing heat changes that occur upon dropping the CofJ$^{4-16}$-GCN4 inhibitory peptide solution into the ΔN28-CofB solution. An exothermic change was observed by dropping the CofJ$^{4-16}$-GCN4 inhibitory peptide solution, which converged to the same level as the heat of dilution as the titration progressed. As a result of analysis of the obtained data using an analysis software Origin, binding of the CofJ$^{4-16}$-GCN4 inhibitory peptide and ΔN28-CofB was observed. The dissociation constant Kd value of both was 0.08 μM.

As a result of analysis, it was shown that the binding affinity between the CofJ$^{4-16}$-GCN4 inhibitory peptide and ΔN28-CofB was stronger about 2.5 times as compared with the binding affinity between CofJ and ΔN28-CofB and it was clarified that the GCN4 fusion type inhibitory peptide efficiently inhibits the interaction between CofJ and ΔN28-CofB.

(Example 13) Inhibition of CofB/CofJ Interaction by CofJ$^{4-16}$-GCN4 Inhibitory Peptide by Pull Down Assay In order to investigate whether the CofJ$^{4-16}$-GCN4 inhibitory peptide can inhibit the binding of CofB and CofJ, it was confirmed in the in vitro experimental system by a pull down assay using a Ni column. For the experiment, ΔN28-CofB (Trx-His-ΔN28-CofB), CofJ and CofJ$^{4-16}$-GCN4, with added thioredoxin tag (Trx) and His tag (His), were used.

Solutions mixed so that the concentration of Trx-His-ΔN28-CofB was 1 μM and the concentration of CofJ$^{4-16}$-GCN4 was (0, 0.5, 1.0, 2.0, 5.0, 10.0 μM) were allowed to stand still on ice overnight. Further, CofJ was mixed so that the final concentration became 1 μM, and the mixtures were allowed to stand still on ice for 1 hour, to obtain experiment samples. Each sample was applied to a Ni column equilibrated with 20 mM Tris-HCl, 150 mM NaCl, pH 8.0, and the column was washed with 20 mM Tris-HCl, 150 mM NaCl, 15 mM Imidazole, pH 8.0. Thereafter, elution was performed with 20 mM Tris-HCl, 150 mM NaCl, 300 mM Imidazole, pH 8.0, and the eluted fraction was confirmed by SDS-PAGE. As a result, it was clarified that the binding of CofJ and Trx-His-ΔN28-CofB can be strongly inhibited by preliminarily mixing CofJ$^{4-16}$-GCN4 having the concentration not lower than that of CofJ with Trx-His-ΔN28-CofB, as shown in FIG. 14.

(Example 14) Evaluation of ETEC Adhesion Inhibitory Activity of CofJ$^{4-16}$-GCN4 Using Caco2 Cells ETEC adhesion inhibitory activity was evaluated in the same manner as in Example 9 using CofJ$^{4-16}$-GCN4.

Mixtures were prepared so that the concentration of CofJ$^{4-16}$-GCN4 was 0, 10, 100, 1000 μg/mL and the concentration of HB101 cof was $1.0 \times 10^9$ cells/mL, then, the mixtures were allowed to stand still at 25° C. for 1 hour, and each 50 μL of the mixtures were added to 500 μL medium so that the concentration of CofJ$^{4-16}$-GCN4 was 0, 1, 10, 100 μg/mL and the concentration of HB101 cof was $1.0 \times 10^8$ cells/mL. As a result, as shown in FIG. 15, the recovery rate was 1.01% for 0 μg/mL CofJ$^{4-16}$-GCN4, 0.32% for 1 μg/mL CofJ$^{4-16}$-GCN4, 0.36% for 10 μg/mL CofJ$^{4-16}$-GCN4 and 0.068% for 100 μg/mL CofJ$^{4-16}$-GCN4.

It was clarified from the results that CofJ$^{4-16}$-GCN4 inhibits colonization of HB101 cof to Caco2 cells in concentration-dependent manner.

What is claimed is:

1. A peptide comprising:
a first domain having an amino acid sequence capable of binding to minor pilin of type IVb pili, and
a second domain having an amino acid sequence connected via a linker sequence to said first domain and capable of multimerizing,
wherein the first domain comprises the sequence of SEQ ID NO: 5 and the second domain comprises the sequence of SEQ ID NO: 6.

2. The peptide according to claim 1, wherein said linker sequence is SEQ ID NO: 9.

3. An inhibitor of colonization of pathogenic bacteria in digestive organs, comprising the peptide according to claim 1.

4. The inhibitor according to claim 3, wherein the pathogenic bacteria comprise enterotoxigenic *Escherichia coli* (ETEC).

5. The peptide according to claim 1, wherein the first domain comprises the sequence of SEQ ID NO:23.

6. A peptide comprising:
a first domain having an amino acid sequence capable of binding to minor pilin of type IVb pili, wherein the first domain comprises the sequence of SEQ ID NO: 5, and wherein the amino acid sequence comprising SEQ ID NO: 5 has up to 24 amino acids in length.

7. The peptide according to claim 6, wherein the first domain comprises the sequence of SEQ ID NO: 23.

8. The peptide according to claim 6, further comprising a second domain having an amino acid sequence connected via a linker sequence to said first domain and capable of multimerizing,
wherein the second domain comprises the sequence of SEQ ID NO: 6.

9. The peptide according to claim 6, further comprising a second domain having an amino acid sequence connected via a linker sequence to said first domain and capable of multimerizing,
wherein the second domain comprises the sequence of SEQ ID NO: 7.

10. The peptide according to claim 6, further comprising a second domain having an amino acid sequence connected via a linker sequence to said first domain and capable of multimerizing,
wherein the second domain comprises the sequence of SEQ ID NO: 8.

* * * * *

SEQUENCE LISTING

```
<160> NUMBER OF SEQ ID NOS: 25

<210> SEQ ID NO 1
<211> LENGTH: 24
<212> TYPE: PRT
<213> ORGANISM: Artificial Sequence
<220> FEATURE:
<223> OTHER INFORMATION: Synthetic

<400> SEQUENCE: 1

Ser Pro Ser Ser Ser Glu Gly Gly Ala Phe Thr Val Asn Met Pro Lys
1               5                   10                  15

Thr Ser Thr Val Asp Asp Ile Arg
            20

<210> SEQ ID NO 2
<211> LENGTH: 25
<212> TYPE: PRT
<213> ORGANISM: Artificial Sequence
<220> FEATURE:
<223> OTHER INFORMATION: Synthetic
```

-continued

```
<400> SEQUENCE: 2

Ser Thr Thr Ser Ser Glu Gly Gly Ala Phe Thr Val Lys Met Ala Lys
1               5                   10                  15

Ser Ser Thr Val Asp Asp Ile Lys Gly
            20                  25

<210> SEQ ID NO 3
<211> LENGTH: 16
<212> TYPE: PRT
<213> ORGANISM: Artificial Sequence
<220> FEATURE:
<223> OTHER INFORMATION: Synthetic

<400> SEQUENCE: 3

Ser Ala Lys Ser Ser Gln Asn Tyr Gly Phe Ser Ala Gly Val Lys Pro
1               5                   10                  15

<210> SEQ ID NO 4
<211> LENGTH: 33
<212> TYPE: PRT
<213> ORGANISM: Artificial Sequence
<220> FEATURE:
<223> OTHER INFORMATION: Synthetic

<400> SEQUENCE: 4

Phe Asn Asp Asn Tyr Ser Ser Thr Ser Thr Val Tyr Ala Thr Ser Asn
1               5                   10                  15

Glu Ala Thr Asp Ser Arg Gly Ser Glu His Leu Arg Tyr Pro Tyr Leu
            20                  25                  30

Glu

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Ser Glu Gly Gly Ala Phe Thr Val Asn Met Pro
1               5                   10

<210> SEQ ID NO 6
<211> LENGTH: 30
<212> TYPE: PRT
<213> ORGANISM: Artificial Sequence
<220> FEATURE:
<223> OTHER INFORMATION: Synthetic

<400> SEQUENCE: 6

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile
            20                  25                  30

<210> SEQ ID NO 7
<211> LENGTH: 3
<212> TYPE: PRT
<213> ORGANISM: Artificial Sequence
<220> FEATURE:
<223> OTHER INFORMATION: Synthetic

<400> SEQUENCE: 7

Pro Pro Gly
```

-continued

<210> SEQ ID NO 8
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is 4Hyp

<400> SEQUENCE: 8

Pro Xaa Gly
1

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Thr Ser Gly Gly Gly
1               5

<210> SEQ ID NO 10
<211> LENGTH: 29
<212> TYPE: DNA
<213> ORGANISM: Artificial Sequence
<220> FEATURE:
<223> OTHER INFORMATION: Synthetic

<400> SEQUENCE: 10
gcgcccgggt cgccatcctc ttcagaagg                               29

<210> SEQ ID NO 11
<211> LENGTH: 34
<212> TYPE: DNA
<213> ORGANISM: Artificial Sequence
<220> FEATURE:
<223> OTHER INFORMATION: Synthetic

<400> SEQUENCE: 11
caagaattct tattaatcaa ggccacaagc cttc                         34

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ggttgcccaa ctttggaaac                                         20

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
acccagaccc gggtccctga aagag                                   25

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
gttccacata tgagcccgtc ttccagcgaa ggtggtgctt tcaccgttaa c          51

<210> SEQ ID NO 15
<211> LENGTH: 55
<212> TYPE: DNA
<213> ORGANISM: Artificial Sequence
<220> FEATURE:
<223> OTHER INFORMATION: Synthetic

<400> SEQUENCE: 15
gacctctact gttgacgata tccgtactag tggtggcggt cgtatgaaac agatc       55

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
gatcgaggaa atcctgtcca agatctacca catcgaaaac gagatcgcgc             50

<210> SEQ ID NO 17
<211> LENGTH: 52
<212> TYPE: DNA
<213> ORGANISM: Artificial Sequence
<220> FEATURE:
<223> OTHER INFORMATION: Synthetic

<400> SEQUENCE: 17
ggatatcgtc aacagtagag gtcttcggca tgttaacggt gaaagcacca cc          52

<210> SEQ ID NO 18
<211> LENGTH: 51
<212> TYPE: DNA
<213> ORGANISM: Artificial Sequence
<220> FEATURE:
<223> OTHER INFORMATION: Synthetic

<400> SEQUENCE: 18
cttggacagg atttcctcga tcttgtcttc gatctgtttc atacgaccgc c           51

<210> SEQ ID NO 19
<211> LENGTH: 52
<212> TYPE: DNA
<213> ORGANISM: Artificial Sequence
<220> FEATURE:
<223> OTHER INFORMATION: Synthetic

<400> SEQUENCE: 19
ctagctctcg agttagataa gcttcttgat acgcgcgatc tcgttttcga tg          52

<210> SEQ ID NO 20
<211> LENGTH: 31
<212> TYPE: DNA
<213> ORGANISM: Artificial Sequence
<220> FEATURE:

```
<223> OTHER INFORMATION: Synthetic

<400> SEQUENCE: 20
gttccaggat ccccgtcttc cagcgaaggt g                                       31

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
ggtgctcgag ttagataagc ttcttg                                             26

<210> SEQ ID NO 22
<211> LENGTH: 24
<212> TYPE: PRT
<213> ORGANISM: Artificial Sequence
<220> FEATURE:
<223> OTHER INFORMATION: Synthetic

<400> SEQUENCE: 22

Asn Pro Ser Gly Phe Asp Lys Ser Gly Ser Ser Thr Thr Arg Thr Pro
  1               5                  10                  15

Ala Met Ser Val Ile Val Asp Glu
            20

<210> SEQ ID NO 23
<211> LENGTH: 13
<212> TYPE: PRT
<213> ORGANISM: Artificial Sequence
<220> FEATURE:
<223> OTHER INFORMATION: Synthetic

<400> SEQUENCE: 23

Ser Ser Glu Gly Gly Ala Phe Thr Val Asn Met Pro Lys
  1               5                  10

<210> SEQ ID NO 24
<211> LENGTH: 42
<212> TYPE: DNA
<213> ORGANISM: Artificial Sequence
<220> FEATURE:
<223> OTHER INFORMATION: Synthetic

<400> SEQUENCE: 24
gatccagcga aggtggtgct ttcaccgtta acatgccgaa ga                           42

<210> SEQ ID NO 25
<211> LENGTH: 42
<212> TYPE: DNA
<213> ORGANISM: Artificial Sequence
<220> FEATURE:
<223> OTHER INFORMATION: Synthetic

<400> SEQUENCE: 25
ctagtcttcg gcatgttaac ggtgaaagca ccaccttcgc tg                           42
```